US008735095B2

(12) United States Patent
Martin et al.

(10) Patent No.: US 8,735,095 B2
(45) Date of Patent: May 27, 2014

(54) HIGH AFFINITY HUMAN ANTIBODIES TO HUMAN IL-4 RECEPTOR

(71) Applicant: Regeneron Pharmaceuticals, Inc., Tarrytown, NY (US)

(72) Inventors: Joel H. Martin, Putnam Valley, NY (US); Tammy T. Huang, Goldens Bridge, NY (US); Jeanette L. Fairhurst, White Plains, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/678,650

(22) Filed: Nov. 16, 2012

(65) Prior Publication Data

US 2013/0078675 A1    Mar. 28, 2013

Related U.S. Application Data

(60) Division of application No. 13/287,151, filed on Nov. 2, 2011, now Pat. No. 8,337,839, which is a division of application No. 12/556,605, filed on Sep. 10, 2009, now Pat. No. 8,075,887, which is a division of application No. 12/260,307, filed on Oct. 29, 2008, now Pat. No. 7,608,693, which is a continuation-in-part of application No. 11/906,517, filed on Oct. 2, 2007, now Pat. No. 7,605,237.

(60) Provisional application No. 60/848,694, filed on Oct. 2, 2006, provisional application No. 60/657,738, filed on Aug. 24, 2007.

(51) Int. Cl.
    C12P 21/08    (2006.01)

(52) U.S. Cl.
    USPC ........ 435/69.1; 435/320.1; 435/325; 435/328; 435/334; 435/358; 435/252.33; 530/387.1; 530/387.3; 530/388.22; 536/23.5

(58) Field of Classification Search
    USPC .............. 530/387.1, 387.3, 388.22; 536/23.5; 435/69.1, 320.1, 325, 328, 334, 358, 435/252.33
    See application file for complete search history.

(56) References Cited

U.S. PATENT DOCUMENTS

| 5,599,905 | A  | 2/1997  | Mosley et al. |
| 5,714,146 | A  | 2/1998  | Lewis et al. |
| 5,717,072 | A  | 2/1998  | Mosley et al. |
| 5,856,296 | A  | 1/1999  | Mosley et al. |
| 5,985,280 | A  | 11/1999 | Ritter et al. |
| 6,156,877 | A  | 12/2000 | Ritter et al. |
| 6,391,581 | B1 | 5/2002  | Mosley et al. |
| 6,716,587 | B2 | 4/2004  | Mosley et al. |
| 7,186,809 | B2 | 3/2007  | Pluenneke |
| 7,317,090 | B2 | 1/2008  | Mosley et al. |
| 7,605,237 | B2 | 10/2009 | Stevens |
| 2005/0255532 | A1 | 11/2005 | Ruben et al. |
| 2005/0282181 | A1 | 12/2005 | Yan et al. |
| 2007/0041976 | A1 | 2/2007  | Pluenneke |
| 2007/0274996 | A1 | 11/2007 | Carter et al. |
| 2009/0074793 | A1 | 3/2009  | Martin et al. |
| 2009/0098142 | A1 | 4/2009  | Kasaian et al. |

FOREIGN PATENT DOCUMENTS

| EP | 0604693 A1 | 7/1994 |
| EP | 0367566 A1 | 5/1997 |
| WO | 01/92340 A2 | 12/2001 |
| WO | WO 01/92340 | 12/2001 |
| WO | 2005047331 A1 | 5/2005 |
| WO | 2005085284 A1 | 9/2005 |
| WO | 2006072564 A1 | 7/2006 |
| WO | 2008054606 A2 | 5/2008 |

OTHER PUBLICATIONS

Ohno, et al. (1985) Proc. Natl. Acad. Sci. USA 82: 2945-2949, "Antigen-binding specificities of antibodies are primarily determined by seven residues of $V_H$".
Davies et al., "Affinity improvement of single antibody VH domains: residues in all three hypervariable regions affect antigen binding," Immunotechnol., 1996, 2(3):169-179.
Holt et al., "Domain antibodies: proteins for therapy," Trends Biotechnol., 2003, 21(11):484-490.
Maliszewski et al., "In vivo biological effects of recombinant soluble interleukin-4 receptor," Proc. Soc. Exp. Biol. Med., 1994, 206(3):233-237.
Sato et al., "Recombinant soluble murine IL-4 receptor can inhibit or enhance IgE responses in vivo," J. Immunol., 1993, 150(7):2717-2723.
Zurawski et al., "The primary binding subunit of the human interleukin-4 receptor is also a component of the interleukin-13 receptor," J. Biol. Chem., 1995, 270(23):13869-13878.
Davis (2004) Seminars in Immunology 16: 239-243, "The evolutionary and structural 'logic' of antigen receptor diversity".
Roitt, et al. (2001) Mosby—Harcourt Publishers Limited, "Immunology—Sixth Edition" pp. 110-111.
Spirin (1986) Vysshaya shkola, Moscow, pp. 17-23, "Molecular Biology Ribosome structure and protein biosynthesis", original Russian article and English language translation of same provided by foreign associate handling local prosecution of Russian application No. 2011120194.
Results of "Search of homology by means of the Internet search shell NCBI Blast®" by Russian Examiner (from corresponding Russian application No. 2011120194) dated Oct. 16, 2013 "for: a) sequence SEQ ID No. 150 . . . b) sequence SEQ ID No. 148 . . . c) sequence SEQ ID No. 156 . . . sequence SEQ ID No. 160".
Results of "Manual search of homology for sequence SEQ ID No. 158" by Russian Examiner (from corresponding Russian application No. 2011120194) dated Oct. 16, 2013.

*Primary Examiner* — Stephen Rawlings
(74) *Attorney, Agent, or Firm* — Swanson & Bratschun, L.L.C.

(57)    ABSTRACT

The present invention provides nucleic acid molecules that encode antibodies or antigen-binding fragments thereof, which specifically bind human interleukin-4 receptor (IL-4R). Also provided are expression vectors comprising nucleic acid molecule that encode anti-IL-4R antibodies, host cells comprising the expression vectors, and methods of producing anti-IL-4R antibodies or antigen-binding fragments thereof comprising growing the host cells under conditions permitting production of the antibody or fragment, and recovering the antibody or fragment so produced.

29 Claims, No Drawings

SEQUENCE LISTING

<160> NUMBER OF SEQ ID NOS: 275

<210> SEQ ID NO 1
<211> LENGTH: 351

-continued

```
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc gtggtccagc ctggagggtc cctgagactc      60
tcctgtgcag cctctggatt caccttccgc tcttatggca tgcactgggt ccgccaggct     120
ccaggcaagg ggctggagtg ggtggcggtc atatcatatg atggaagtaa taaatattat     180
atagactccg tgaagggccg attcaccatc tccagagaca attccaagaa cacgctgaat     240
ctgcaaatga acagcctgag acttgaggac acggctgtat attactgtgc gaaagagggg     300 aggggggggat ttgactactg gggccaggga atcccggtca ccgtctcctc a             351

<210> SEQ ID NO 2
<211> LENGTH: 117
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ile Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Leu Glu Asp Thr Ala Val Tyr Tyr Cys
                85                  90                  95

Ala Lys Glu Gly Arg Gly Gly Phe Asp Tyr Trp Gly Gln Gly Ile Pro
            100                 105                 110

Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tccgctctta tggc                                             24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Arg Ser Tyr Gly
 1               5

<210> SEQ ID NO 5
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatcatatg atggaagtaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Tyr Asp Gly Ser Asn Lys
 1               5

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
gcgaaagagg ggagggggg atttgactac                                    30

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Ala Lys Glu Gly Arg Gly Gly Phe Asp Tyr
 1               5                  10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctca ctgtctgcat ctgtaggaga cagagtcacc    60
atcacttgtc gggcgagtca ggtcataaac aattatttag cctggtttca gcagaaacca   120
gggaaagtcc ctaagtccct gatccatgct gcatccagtt tacaaagtgg ggtcccatca   180
aagttcagcg gcagtggatc tgggacagat ttcactctca ccatcagcag cctgcagcct   240
gaagattttg caacttatta ctgccaacag tataatagtc acccgtggac gttcggccaa   300
gggaccaagg tggaaatcaa acga                                         324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Val Ile Asn Asn Tyr
             20                  25                  30

Leu Ala Trp Phe Gln Lys Pro Gly Lys Val Pro Lys Ser Leu Ile
             35                  40                  45

His Ala Ala Ser Ser Leu Gln Ser Gly Val Pro Ser Lys Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
caggtcataa acaattat                                               18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Val Ile Asn Asn Tyr
 1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                          9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Ala Ala Ser
 1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagtata atagtcaccc gtggacg          27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Ser His Pro Trp Thr
1               5

<210> SEQ ID NO 17
<211> LENGTH: 351
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctggagggtc cctgagactc     60
tcctgtgcag cctctggatt caccttccgc tcttatggca tgcactgggt ccgccaggct    120
ccaggcaagg ggctggagtg ggtggcggtc atatcatatg atggaagtaa taaatattat    180
atagactccg tgaagggccg attcaccatc tccagagaca attccaagaa cacgctgaat    240
ctgcaaatga acagcctgag acttgaggac acggctgtat attactgtgc gaaagagggg    300 aggggggat tgactactg gggccaggga accctggtca ccgtctcctc a              351

<210> SEQ ID NO 18
<211> LENGTH: 117
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ile Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Leu Glu Asp Thr Ala Val Tyr Tyr Cys
                85                  90                  95

Ala Lys Glu Gly Arg Gly Gly Phe Asp Tyr Trp Gly Gln Gly Thr Leu
            100                 105                 110

Val Thr Val Ser Ser
        115

<210> SEQ ID NO 19
<211> LENGTH: 321
<212> TYPE: DNA
<213> ORGANISM: Artificial Sequence
<220> FEATURE:
<223> OTHER INFORMATION: Synthetic

<400> SEQUENCE: 19

```
gacatccaga tgacccagtc tccatcctca ctgtctgcat ctgtaggaga cagagtcacc    60
atcacttgtc gggcgagtca ggtcataaac aattatttag cctggtttca gcagaaacca   120
gggaaagtcc ctaagtccct gatccatgct gcatccagtt tacaaagtgg ggtcccatca   180
aagttcagcg gcagtggatc tgggacagat ttcactctca ccatcagcag cctgcagcct   240
gaagattttg caacttatta ctgccaacag tataatagtc acccgtggac gttcggccaa   300
gggaccaagg tggaaatcaa a                                             321
```

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Val Ile Asn Asn Tyr
             20                  25                  30
Leu Ala Trp Phe Gln Gln Lys Pro Gly Lys Val Pro Lys Ser Leu Ile
         35                  40                  45
His Ala Ala Ser Ser Leu Gln Ser Gly Val Pro Ser Lys Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser His Pro Trp
                 85                  90                  95
Thr Phe Gly Gln Gly Thr Lys Val Glu Ile Lys
                100                 105
```

<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21

```
caggtgcagc tggtggagtc tgggggaggc gtggtccagc ctggggaggtc cctgagactc    60
tcctgtgcag cctctggatt caccttccgc tcttatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagagggg   300
aggggggat tgactactg gggccaggga accctggtca ccgtctcctc a              351
```

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

```
Gln Val Gln Leu Val Glu Ser Gly Gly Gly Val Val Gln Pro Gly Arg
  1               5                  10                  15
```

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Arg Gly Gly Phe Asp Tyr Trp Gly Gln Gly Thr Leu
            100                 105                 110

Val Thr Val Ser Ser
        115

<210> SEQ ID NO 23
<211> LENGTH: 322
<212> TYPE: DNA
<213> ORGANISM: Artificial Sequence
<220> FEATURE:
<223> OTHER INFORMATION: Synthetic

<400> SEQUENCE: 23
gacatccaga tgacccagtc tccatcctca ctgtctgcat ctgtaggaga cagagtcacc      60
atcacttgtc gggcgagtca ggtcataaac aattatttag cctggtttca gcagaaacca     120
gggaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtc acccgtggac gttcggccaa     300
gggaccaagg tggaaatcaa ac                                              322

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105

<210> SEQ ID NO 25
<211> LENGTH: 351
<212> TYPE: DNA
<213> ORGANISM: Artificial Sequence
<220> FEATURE:

-continued

<223> OTHER INFORMATION: Synthetic

<400> SEQUENCE: 25

```
caggtgcagc tggtggagtc tgggggaggc gtggtccagc ctggagggtc cctgagactc    60
tcctgtgcag cctctggatt caccttcaga agctatggca tacactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacactgtat   240
ctgcaaatga acagcctgat aactgaggac acggctgtgt attattgtgt gaaagagggg   300
agggggggt tgactactg gggccaggga accacggtca ccgtctcctc a              351
```

<210> SEQ ID NO 26
<211> LENGTH: 117
<212> TYPE: PRT
<213> ORGANISM: Artificial Sequence
<220> FEATURE:
<223> OTHER INFORMATION: Synthetic

<400> SEQUENCE: 26

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Gly Ile His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Ile Thr Glu Asp Thr Ala Val Tyr Tyr Cys
                 85                  90                  95

Val Lys Glu Gly Arg Gly Gly Phe Asp Tyr Trp Gly Gln Gly Thr Thr
            100                 105                 110

Val Thr Val Ser Ser
        115
```

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27

```
ggattcacct tcagaagcta tggc                                            24
```

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

```
Gly Phe Thr Phe Arg Ser Tyr Gly
  1               5
```

<210> SEQ ID NO 29
<211> LENGTH: 24
<212> TYPE: DNA
<213> ORGANISM: Artificial Sequence

```
<220> FEATURE:
<223> OTHER INFORMATION: Synthetic

<400> SEQUENCE: 29
atatcatatg atggaagtaa taaa                                              24

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Ser Tyr Asp Gly Ser Asn Lys
1               5

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
gtgaaagagg ggaggggggg gtttgactac                                        30

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Val Lys Glu Gly Arg Gly Gly Phe Asp Tyr
1               5                  10

<210> SEQ ID NO 33
<211> LENGTH: 324
<212> TYPE: DNA
<213> ORGANISM: Artificial Sequence
<220> FEATURE:
<223> OTHER INFORMATION: Synthetic

<400> SEQUENCE: 33
gacatccaga tgacccagtc tccatcctca ctgtctgcat ctgtaggaga cagagtcacc       60
atcacttgtc gggcgagtca ggtcattaat aattatttag cctggtttca gcagaaacca      120
gggaaagtcc ctaagtccct gatccatgct gcatccagtt tgcaaagagg gtcccatca       180 aagttcagcg gcagtggatc tgggacagat ttcactctca ccatcaacag cctgcagcct      240
gaagattttg caacttatta ctgccaacaa tataatagtt acccgtggac gttcggccaa      300
gggaccaagg tggaaatcaa acga                                             324

<210> SEQ ID NO 34
<211> LENGTH: 108
<212> TYPE: PRT
<213> ORGANISM: Artificial Sequence
<220> FEATURE:
<223> OTHER INFORMATION: Synthetic

<400> SEQUENCE: 34

Asp Ile Gln Met Thr Gln Ser Pro Ser Ser Leu Ser Ala Ser Val Gly
1               5                  10                  15
```

```
Asp Arg Val Thr Ile Thr Cys Arg Ala Ser Gln Val Ile Asn Asn Tyr
            20                  25                  30
Leu Ala Trp Phe Gln Gln Lys Pro Gly Lys Val Pro Lys Ser Leu Ile
         35                  40                  45
His Ala Ala Ser Ser Leu Gln Arg Gly Val Pro Ser Lys Phe Ser Gly
     50                  55                  60
Ser Gly Ser Gly Thr Asp Phe Thr Leu Thr Ile Asn Ser Leu Gln Pro
 65                  70                  75                  80
Glu Asp Phe Ala Thr Tyr Tyr Cys Gln Gln Tyr Asn Ser Tyr Pro Trp
                 85                  90                  95
Thr Phe Gly Gln Gly Thr Lys Val Glu Ile Lys Arg
            100                 105
```

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
caggtcatta ataattat                                                18

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Val Ile Asn Asn Tyr
 1               5

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37 gctgcatcc                                                           9

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Ala Ala Ser
 1

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
caacaatata atagttaccc gtggacg                                       27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Gln Gln Tyr Asn Ser Tyr Pro Trp Thr
 1               5

<210> SEQ ID NO 41
<211> LENGTH: 351
<212> TYPE: DNA
<213> ORGANISM: Artificial Sequence
<220> FEATURE:
<223> OTHER INFORMATION: Synthetic

<400> SEQUENCE: 41
caggtgcagc tggtggagtc tgggggaggc gtggtccagc ctggggaggtc cctgagactc      60 tcctgtgcag cctctggatt caccttcaga agctatggca tacactgggt ccgccaggct     120
ccaggcaagg gctggagtg gtggcagtt atatcatatg atggaagtaa taaatactat      180
gcagactccg tgaagggccg attcaccatc tccagagaca attccaagaa cacactgtat     240
ctgcaaatga acagcctgat aactgaggac acggctgtgt attattgtgt gaaagagggg     300 agggggggt tgactactg gggccaggga accctggtca ccgtctcctc a              351

<210> SEQ ID NO 42
<211> LENGTH: 117
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Ile Thr Glu Asp Thr Ala Val Tyr Tyr Cys
                85                  90                  95

Val Lys Glu Gly Arg Gly Gly Phe Asp Tyr Trp Gly Gln Gly Thr Leu
            100                 105                 110

Val Thr Val Ser Ser
        115

<210> SEQ ID NO 43
<211> LENGTH: 321
<212> TYPE: DNA
<213> ORGANISM: Artificial Sequence
<220> FEATURE:
<223> OTHER INFORMATION: Synthetic

<400> SEQUENCE: 43
gacatccaga tgacccagtc tccatcctca ctgtctgcat ctgtaggaga cagagtcacc      60

```
atcacttgtc gggcgagtca ggtcattaat aattatttag cctggtttca gcagaaacca    120
gggaaagtcc ctaagtccct gatccatgct gcatccagtt tgcaaagagg ggtcccatca    180
aagttcagcg gcagtggatc tgggacagat ttcactctca ccatcaacag cctgcagcct    240
gaagattttg caacttatta ctgccaacaa tataatagtt acccgtggac gttcggccaa    300
gggaccaagg tggaaatcaa a                                              321
```

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Val Ile Asn Asn Tyr
             20                  25                  30

Leu Ala Trp Phe Gln Gln Lys Pro Gly Lys Val Pro Lys Ser Leu Ile
         35                  40                  45

His Ala Ala Ser Ser Leu Gln Arg Gly Val Pro Ser Lys Phe Ser Gly
     50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Tyr Asn Ser Tyr Pro Trp
                 85                  90                  95

Thr Phe Gly Gln Gly Thr Lys Val Glu Ile Lys
            100                 105
```

<210> SEQ ID NO 45
<211> LENGTH: 351
<212> TYPE: DNA
<213> ORGANISM: Artificial Sequence
<220> FEATURE:
<223> OTHER INFORMATION: Synthetic

<400> SEQUENCE: 45

```
caggtgcagc tggtggagtc tgggggaggc gtggtccagc ctggggaggtc cctgagactc    60 tcctgtgcag cctctggatt caccttcaga agctatggca tgcactgggt ccgccaggct   120
ccaggcaagg ggctggagtg gtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgt gaaagagggg   300 agggggggggt tgactactg gggccaggga accctggtca ccgtctcctc a            351
```

<210> SEQ ID NO 46
<211> LENGTH: 117
<212> TYPE: PRT
<213> ORGANISM: Artificial Sequence
<220> FEATURE:
<223> OTHER INFORMATION: Synthetic

<400> SEQUENCE: 46

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
             20                  25                  30
```

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Glu Gly Arg Gly Gly Phe Asp Tyr Trp Gly Gln Gly Thr Leu
            100                 105                 110

Val Thr Val Ser Ser
            115

<210> SEQ ID NO 47
<211> LENGTH: 322
<212> TYPE: DNA
<213> ORGANISM: Artificial Sequence
<220> FEATURE:
<223> OTHER INFORMATION: Synthetic

<400> SEQUENCE: 47
gacatccaga tgacccagtc tccatcctca ctgtctgcat ctgtaggaga cagagtcacc      60
atcacttgtc gggcgagtca ggtcattaat aattatttag cctggtttca gcagaaacca     120
gggaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacaa tataatagtt acccgtggac gttcggccaa     300
gggaccaagg tggaaatcaa ac                                              322

<210> SEQ ID NO 48
<211> LENGTH: 107
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Val Ile Asn Asn Tyr
             20                  25                  30

Leu Ala Trp Phe Gln Lys Pro Gly Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Trp
                 85                  90                  95

Thr Phe Gly Gln Gly Thr Lys Val Glu Ile Lys
            100                 105

<210> SEQ ID NO 49
<211> LENGTH: 375
<212> TYPE: DNA
<213> ORGANISM: Artificial Sequence
<220> FEATURE:
<223> OTHER INFORMATION: Synthetic

<400> SEQUENCE: 49

```
caggtgcagc tggtggagtc tggggggaggc ttggaacagc cggggggtc cttgagactc    60 tcctgtgcag gctctggatt cacgtttaga gactatgcca tgacctgggt ccgccaggct   120
ccagggaagg gctggagtg gtcgcatcg attagtggtt ccgtggtaa cacatacttc     180 gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattat ggtttggacg tctggggcca agggtccacg   360
gtcaccgtct cctca                                                    375
```

<210> SEQ ID NO 50
<211> LENGTH: 125
<212> TYPE: PRT
<213> ORGANISM: Artificial Sequence
<220> FEATURE:
<223> OTHER INFORMATION: Synthetic
<400> SEQUENCE: 50

```
Gln Val Gln Leu Val Glu Ser Gly Gly Gly Leu Glu Gln Pro Gly Gly
  1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ala Ser Ile Ser Gly Ser Gly Gly Asn Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125
```

<210> SEQ ID NO 51
<211> LENGTH: 24
<212> TYPE: DNA
<213> ORGANISM: Artificial Sequence
<220> FEATURE:
<223> OTHER INFORMATION: Synthetic
<400> SEQUENCE: 51

```
ggattcacgt ttagagacta tgcc                                           24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic
<400> SEQUENCE: 52

```
Gly Phe Thr Phe Arg Asp Tyr Ala
  1               5
```

<210> SEQ ID NO 53
<211> LENGTH: 24
<212> TYPE: DNA
<213> ORGANISM: Artificial Sequence
<220> FEATURE:

<223> OTHER INFORMATION: Synthetic

<400> SEQUENCE: 53
attagtggtt ccggtggtaa caca                                         24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Gly Ser Gly Gly Asn Thr
1               5

<210> SEQ ID NO 55
<211> LENGTH: 54
<212> TYPE: DNA
<213> ORGANISM: Artificial Sequence
<220> FEATURE:
<223> OTHER INFORMATION: Synthetic

<400> SEQUENCE: 55
gcgaaagatc gactctctat aacaattcgc ccacgctatt atggtttgga cgtc        54

<210> SEQ ID NO 56
<211> LENGTH: 18
<212> TYPE: PRT
<213> ORGANISM: Artificial Sequence
<220> FEATURE:
<223> OTHER INFORMATION: Synthetic

<400> SEQUENCE: 56

Ala Lys Asp Arg Leu Ser Ile Thr Ile Arg Pro Arg Tyr Tyr Gly Leu
1               5                  10                  15

Asp Val

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctca ctgtctgcat ctgttggaga cagagtcacc    60
atcacttgtc gggcgagtca ggccattaac aatcatttag cctggtttca gcagaaacca   120
gggaaagccc ctaagtccct gatctttgct gtatccagtt tgcaaagtgg ggtcccatca   180
aagttcagcg gcagtggatc tgggacagac ttcactctca ccatcagcag cctgcagcct   240
gaagattttg caacttatta ctgccaacag tataatagtt acccgtggac gttcggccaa   300
gggaccaagg tggaaatcaa acga                                         324

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1               5                  10                  15

```
Asp Arg Val Thr Ile Thr Cys Arg Ala Ser Gln Ala Ile Asn Asn His
            20                  25                  30

Leu Ala Trp Phe Gln Gln Lys Pro Gly Lys Ala Pro Lys Ser Leu Ile
        35                  40                  45

Phe Ala Val Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys Arg
            100                 105
```

```
<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggccatta acaatcat                                                    18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ala Ile Asn Asn His
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgtatcc                                                               9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Val Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttaccc gtggacg                                          27
```

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Pro Trp Thr
1               5

<210> SEQ ID NO 65
<211> LENGTH: 372
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggaacagc cggggggggtc cttgagactc      60 tcctgtgcag gctctggatt cacgtttaga gactatgcca tgacctgggt ccgccaggct     120
ccagggaagg ggctggagtg gtcgcatcg attagtggtt ccggtggtaa cacatacttc     180
gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattat ggtttggacg tctggggcca agggaccacg     360
gtcaccgtct cc                                                         372

<210> SEQ ID NO 66
<211> LENGTH: 124
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ala Ser Ile Ser Gly Ser Gly Gly Asn Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67

```
gacatccaga tgacccagtc tccatcctca ctgtctgcat ctgttggaga cagagtcacc    60
atcacttgtc gggcgagtca ggccattaac aatcatttag cctggtttca gcagaaacca   120
gggaaagccc ctaagtccct gatctttgct gtatccagtt tgcaaagtgg ggtcccatca   180
aagttcagcg gcagtggatc tgggacagac ttcactctca ccatcagcag cctgcagcct   240
gaagattttg caacttatta ctgccaacag tataatagtt acccgtggac gttcggccaa   300
gggaccaagg tggaaatcaa a                                             321
```

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ala Ile Asn Asn His
             20                  25                  30
Leu Ala Trp Phe Gln Gln Lys Pro Gly Lys Ala Pro Lys Ser Leu Ile
         35                  40                  45
Phe Ala Val Ser Ser Leu Gln Ser Gly Val Pro Ser Lys Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser Tyr Pro Trp
                 85                  90                  95
Thr Phe Gly Gln Gly Thr Lys Val Glu Ile Lys
            100                 105
```

<210> SEQ ID NO 69
<211> LENGTH: 373
<212> TYPE: DNA
<213> ORGANISM: Artificial Sequence
<220> FEATURE:
<223> OTHER INFORMATION: Synthetic

<400> SEQUENCE: 69

```
gaggtgcagc tggtggagtc tgggggaggc ttggtacagc ctgggggatc cctgagactc    60
tcctgtgcag cctctggatt cacgtttaga gactatgcca tgagctgggt ccgccaggct   120
ccagggaagg ggctggagtg ggtctcagct attagtggtt ccgtggtaa  cacatactac   180
gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattat ggtttggacg tctggggcca agggaccacg   360
gtcaccgtct cct                                                      373
```

<210> SEQ ID NO 70
<211> LENGTH: 124
<212> TYPE: PRT
<213> ORGANISM: Artificial Sequence
<220> FEATURE:
<223> OTHER INFORMATION: Synthetic

<400> SEQUENCE: 70

```
Glu Val Gln Leu Val Glu Ser Gly Gly Gly Leu Val Gln Pro Gly Gly
```

```
                1               5                  10                 15
Ser Leu Arg Leu Ser Cys Ala Ala Ser Gly Phe Thr Phe Arg Asp Tyr
            20                  25                 30

Ala Met Ser Trp Val Arg Gln Ala Pro Gly Lys Gly Leu Glu Trp Val
            35                  40                 45

Ser Ala Ile Ser Gly Ser Gly Gly Asn Thr Tyr Tyr Ala Asp Ser Val
            50                  55                 60

Lys Gly Arg Phe Thr Ile Ser Arg Asp Asn Ser Lys Asn Thr Leu Tyr
65                              70                 75                 80

Leu Gln Met Asn Ser Leu Arg Ala Glu Asp Thr Ala Val Tyr Tyr Cys
                85                  90                 95

Ala Lys Asp Arg Leu Ser Ile Thr Ile Arg Pro Arg Tyr Tyr Gly Leu
                100                 105                110

Asp Val Trp Gly Gln Gly Thr Thr Val Thr Val Ser
            115                 120
```

<210> SEQ ID NO 71
<211> LENGTH: 322
<212> TYPE: DNA
<213> ORGANISM: Artificial Sequence
<220> FEATURE:
<223> OTHER INFORMATION: Synthetic

<400> SEQUENCE: 71

```
gacatccaga tgacccagtc tccatcctca ctgtctgcat ctgtaggaga cagagtcacc    60
atcacttgtc gggcgagtca ggccattaac aatcatttag cctggtttca gcagaaacca   120
gggaaagccc ctaagtccct gatctatgct gtatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgtggac gttcggccaa   300
gggaccaagg tggaaatcaa ac                                            322
```

<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn His
            20                  25                  30

Leu Ala Trp Phe Gln Gln Lys Pro Gly Lys Ala Pro Lys Ser Leu Ile
            35                  40                  45

Tyr Ala Val Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                              70                  75                 80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105
```

<210> SEQ ID NO 73
<211> LENGTH: 375
<212> TYPE: DNA

```
<213> ORGANISM: Artificial Sequence
<220> FEATURE:
<223> OTHER INFORMATION: Synthetic

<400> SEQUENCE: 73
caggtgcagc tggtggagtc tgggggaggc ttggaacagc cggggggtc cttgagactc      60 tcctgtgcag gctctggatt cacgtttaga gactatgcca tgacctgggt ccgccaggct    120
ccagggaagg gctggagtg gtcgcatcg attagtggtt ccggtggtaa cacatacttc      180
gcagactccg tgaagggccg gttcaccatc tccagagaca attccaagaa cacgctgtat    240
ctgcaaatga acagcctgag agccgaggac acggccgtat attactgtgc gaaagatcga    300
ctctctataa caattcgccc acgctattat ggtttggacg tctggggcca agggtccacg    360
gtcaccgtct cctca                                                      375

<210> SEQ ID NO 74
<211> LENGTH: 125
<212> TYPE: PRT
<213> ORGANISM: Artificial Sequence
<220> FEATURE:
<223> OTHER INFORMATION: Synthetic

<400> SEQUENCE: 74

Gln Val Gln Leu Val Glu Ser Gly Gly Gly Leu Glu Gln Pro Gly Gly
  1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ala Ser Ile Ser Gly Ser Gly Gly Asn Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
ggattcacgt ttagagacta tgcc                                             24

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Arg Asp Tyr Ala
  1               5
```

```
<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77
attagtggtt ccggtggtaa caca                                       24

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Gly Ser Gly Gly Asn Thr
 1               5

<210> SEQ ID NO 79
<211> LENGTH: 54
<212> TYPE: DNA
<213> ORGANISM: Artificial Sequence
<220> FEATURE:
<223> OTHER INFORMATION: Synthetic

<400> SEQUENCE: 79
gcgaaagatc gactctctat aacaattcgc ccacgctatt atggtttgga cgtc      54

<210> SEQ ID NO 80
<211> LENGTH: 18
<212> TYPE: PRT
<213> ORGANISM: Artificial Sequence
<220> FEATURE:
<223> OTHER INFORMATION: Synthetic

<400> SEQUENCE: 80

Ala Lys Asp Arg Leu Ser Ile Thr Ile Arg Pro Arg Tyr Tyr Gly Leu
 1               5                  10                  15

Asp Val

<210> SEQ ID NO 81
<211> LENGTH: 339
<212> TYPE: DNA
<213> ORGANISM: Artificial Sequence
<220> FEATURE:
<223> OTHER INFORMATION: Synthetic

<400> SEQUENCE: 81
gaaatagtgt tgacgcagtc tccactctcc ctgcccgtca cccctggaga gccggcctcc    60
atctcctgca ggtctagtca gagcctcctg tatagtattg atacaacta tttggattgg   120 tacctgcaga agtcagggca gtctccacag ctccttatct atttgggttc taatcgggcc   180
tccggggtcc ctgacaggtt cagtggcagt ggatcaggca cagattttac actgaaaatc   240
agcagagtgg aggctgagga tgttggggttt tattactgca tgcaagctct acaaactccg   300 tacactttg ccccggggac caagctggag atcaaacga                           339

<210> SEQ ID NO 82
<211> LENGTH: 113
<212> TYPE: PRT
<213> ORGANISM: Artificial Sequence
<220> FEATURE:
<223> OTHER INFORMATION: Synthetic
```

<400> SEQUENCE: 82

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Pro Gly Thr Lys Leu Glu Ile Lys
            100                 105                 110

Arg

<210> SEQ ID NO 83
<211> LENGTH: 33
<212> TYPE: DNA
<213> ORGANISM: Artificial Sequence
<220> FEATURE:
<223> OTHER INFORMATION: Synthetic

<400> SEQUENCE: 83
cagagcctcc tgtatagtat tggatacaac tat                                33

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

Gln Ser Leu Leu Tyr Ser Ile Gly Tyr Asn Tyr
1               5                   10

<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85 ttgggttct                                                           9

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Leu Gly Ser
1

<210> SEQ ID NO 87
<211> LENGTH: 27
<212> TYPE: DNA

```
<213> ORGANISM: Artificial Sequence
<220> FEATURE:
<223> OTHER INFORMATION: Synthetic

<400> SEQUENCE: 87
atgcaagctc tacaaactcc gtacact                                            27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Met Gln Ala Leu Gln Thr Pro Tyr Thr
 1               5

<210> SEQ ID NO 89
<211> LENGTH: 372
<212> TYPE: DNA
<213> ORGANISM: Artificial Sequence
<220> FEATURE:
<223> OTHER INFORMATION: Synthetic

<400> SEQUENCE: 89
gaggtgcagc tggtggagtc tgggggaggc ttggaacagc cggggggggtc cttgagactc      60 tcctgtgcag gctctggatt cacgtttaga gactatgcca tgacctgggt ccgccaggct     120
ccagggaagg gctggagtg gtcgcatcg attagtggtt ccgtggtaa cacatacttc        180 gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattat ggtttggacg tctggggcca agggaccacg     360
gtcaccgtct cc                                                         372

<210> SEQ ID NO 90
<211> LENGTH: 124
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Glu Gln Pro Gly Gly
 1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ala Ser Ile Ser Gly Ser Gly Gly Asn Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 91
<211> LENGTH: 336
<212> TYPE: DNA
<213> ORGANISM: Artificial Sequence
<220> FEATURE:
<223> OTHER INFORMATION: Synthetic

<400> SEQUENCE: 91

```
gatattgtga tgactcagtc tccactctcc ctgcccgtca cccctggaga gccggcctcc      60
atctcctgca ggtctagtca gagcctcctg tatagtattg atacaacta tttggattgg     120
tacctgcaga agtcaggca gtctccacag ctccttatct atttgggttc taatcgggcc     180
tccggggtcc ctgacaggtt cagtggcagt ggatcaggca cagattttac actgaaaatc     240
agcagagtgg aggctgagga tgttgggttt tattactgca tgcaagctct acaaactccg     300
tacactttg gccgggac caagctggag atcaaa                                 336
```

<210> SEQ ID NO 92
<211> LENGTH: 112
<212> TYPE: PRT
<213> ORGANISM: Artificial Sequence
<220> FEATURE:
<223> OTHER INFORMATION: Synthetic

<400> SEQUENCE: 92

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Pro Gly Thr Lys Leu Glu Ile Lys
            100                 105                 110
```

<210> SEQ ID NO 93
<211> LENGTH: 373
<212> TYPE: DNA
<213> ORGANISM: Artificial Sequence
<220> FEATURE:
<223> OTHER INFORMATION: Synthetic

<400> SEQUENCE: 93

```
gaggtgcagc tggtggagtc tgggggaggc ttggtacagc ctggggggtc cctgagactc      60
tcctgtgcag cctctggatt cacgtttaga gactatgcca tgagctgggt ccgccaggct     120
ccagggaagg gctggagtg gtctcagct attagtggtt ccggtggtaa cacatactac     180
gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattat ggtttggacg tctggggcca agggaccacg     360
gtcaccgtct cct                                                      373
```

<210> SEQ ID NO 94
<211> LENGTH: 124
<212> TYPE: PRT

<213> ORGANISM: Artificial Sequence
<220> FEATURE:
<223> OTHER INFORMATION: Synthetic

<400> SEQUENCE: 94

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Arg | Asp | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Ser | Gly | Gly | Asn | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Asp | Arg | Leu | Ser | Ile | Thr | Ile | Arg | Pro | Arg | Tyr | Tyr | Gly | Leu |
| | | | 100 | | | | | 105 | | | | | 110 | | |
| Asp | Val | Trp | Gly | Gln | Gly | Thr | Thr | Val | Thr | Val | Ser | | | | |
| | | 115 | | | | | 120 | | | | | | | | |

<210> SEQ ID NO 95
<211> LENGTH: 337
<212> TYPE: DNA
<213> ORGANISM: Artificial Sequence
<220> FEATURE:
<223> OTHER INFORMATION: Synthetic

<400> SEQUENCE: 95

```
gatattgtga tgactcagtc tccactctcc ctgcccgtca cccctggaga gccggcctcc      60
atctcctgca ggtctagtca gagcctcctg tatagtattg atacaacta  tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttgggggtt tattactgca tgcaagctct acaaactccg    300
tacactttg  gccaggggac caagctggag atcaaac                              337
```

<210> SEQ ID NO 96
<211> LENGTH: 112
<212> TYPE: PRT
<213> ORGANISM: Artificial Sequence
<220> FEATURE:
<223> OTHER INFORMATION: Synthetic

<400> SEQUENCE: 96

| | | | | | | | | | | | | | | |
|---|---|---|---|---|---|---|---|---|---|---|---|---|---|---|
| Asp | Ile | Val | Met | Thr | Gln | Ser | Pro | Leu | Ser | Leu | Pro | Val | Thr | Pro | Gly |
| 1 | | | | 5 | | | | | 10 | | | | | 15 | |
| Glu | Pro | Ala | Ser | Ile | Ser | Cys | Arg | Ser | Ser | Gln | Ser | Leu | Leu | Tyr | Ser |
| | | | 20 | | | | | 25 | | | | | 30 | | |
| Ile | Gly | Tyr | Asn | Tyr | Leu | Asp | Trp | Tyr | Leu | Gln | Lys | Pro | Gly | Gln | Ser |
| | | 35 | | | | | 40 | | | | | 45 | | | |
| Pro | Gln | Leu | Leu | Ile | Tyr | Leu | Gly | Ser | Asn | Arg | Ala | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Met | Gln | Ala |
| | | | | 85 | | | | | 90 | | | | | 95 | |

```
Leu Gln Thr Pro Tyr Thr Phe Gly Gln Gly Thr Lys Leu Glu Ile Lys
                100                 105                 110
```

<210> SEQ ID NO 97
<211> LENGTH: 375
<212> TYPE: DNA
<213> ORGANISM: Artificial Sequence
<220> FEATURE:
<223> OTHER INFORMATION: Synthetic

<400> SEQUENCE: 97

```
caggtgcagc tggtggagtc tgagggactc ttggaacagc ctggggggtc cctgagactc     60
tcctgtgcag cctctggatt caactttaga gactttgcca tgacctgggt ccgccaggct    120
ccagggaagg gctggagtg gtctcatct attagtggta gtggtagtaa tacatactac      180
gcagactccg tgaagggccg gttcaccatc tccagagaca attccaacca cacgctgtat    240
ctgcgaatga acagcctgag agccgaagac acggccgtgt attactgtgc gaaagatcga    300
ctctctataa caattcgccc acgctattac ggtctggacg tctggggcca agggtccacg    360
gtcaccgtct cctca                                                     375
```

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

```
Gln Val Gln Leu Val Glu Ser Glu Gly Leu Leu Glu Gln Pro Gly Gly
  1               5                  10                  15
Ser Leu Arg Leu Ser Cys Ala Ala Ser Gly Phe Asn Phe Arg Asp Phe
             20                  25                  30
Ala Met Thr Trp Val Arg Gln Ala Pro Gly Lys Gly Leu Glu Trp Val
         35                  40                  45
Ser Ser Ile Ser Gly Ser Gly Ser Asn Thr Tyr Tyr Ala Asp Ser Val
     50                  55                  60
Lys Gly Arg Phe Thr Ile Ser Arg Asp Asn Ser Asn His Thr Leu Tyr
 65                  70                  75                  80
Leu Arg Met Asn Ser Leu Arg Ala Glu Asp Thr Ala Val Tyr Tyr Cys
                 85                  90                  95
Ala Lys Asp Arg Leu Ser Ile Thr Ile Arg Pro Arg Tyr Tyr Gly Leu
            100                 105                 110
Asp Val Trp Gly Gln Gly Ser Thr Val Thr Val Ser Ser
        115                 120                 125
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcaact ttagagactt tgcc                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Asn Phe Arg Asp Phe Ala
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggta gtggtagtaa taca                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Ser Gly Ser Asn Thr
1               5

<210> SEQ ID NO 103
<211> LENGTH: 54
<212> TYPE: DNA
<213> ORGANISM: Artificial Sequence
<220> FEATURE:
<223> OTHER INFORMATION: Synthetic

<400> SEQUENCE: 103
gcgaaagatc gactctctat aacaattcgc ccacgctatt acggtctgga cgtc         54

<210> SEQ ID NO 104
<211> LENGTH: 18
<212> TYPE: PRT
<213> ORGANISM: Artificial Sequence
<220> FEATURE:
<223> OTHER INFORMATION: Synthetic

<400> SEQUENCE: 104

Ala Lys Asp Arg Leu Ser Ile Thr Ile Arg Pro Arg Tyr Tyr Gly Leu
1               5                   10                  15

Asp Val

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc    60
atcacttgcc gggcgagtca ggacattagc aattattttg cctggtatca gcagaagcca   120
gggaaagttc ctaagctcct gatctttgct gcatccactt tgcatccagg ggtcccatct   180
cggttcagtg gcagtggatc tgggacagat ttcactctca ccattcgcag cctgcagcct   240
gaagatgttg caacttatta ctgtcaaaaa tatgacagtg ccccgtacac ttttggccag   300
gggaccaagg tggaaatcaa acga                                         324

```
<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Val Pro Lys Leu Leu Ile
        35                  40                  45

Phe Ala Ala Ser Thr Leu His Pro Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Val Ala Thr Tyr Tyr Cys Gln Lys Tyr Asp Ser Ala Pro Tyr
                85                  90                  95

Thr Phe Gly Gln Gly Thr Lys Val Glu Ile Lys Arg
            100                 105

```
<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gcaattat                                              18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108
```

Gln Asp Ile Ser Asn Tyr
1               5

```
<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                         9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110
```

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caaaaatatg acagtgcccc gtacact                                          27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Lys Tyr Asp Ser Ala Pro Tyr Thr
 1               5

<210> SEQ ID NO 113
<211> LENGTH: 372
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgagggactc ttggaacagc tgggggggtc cctgagactc        60
tcctgtgcag cctctggatt caactttaga gactttgcca tgacctgggt ccgccaggct       120
ccagggaagg ggctggagtg ggtctcatct attagtggta gtggtagtaa tacatactac       180
gcagactccg tgaagggccg gttcaccatc tccagagaca attccaacca cacgctgtat       240
ctgcgaatga acagcctgag agccgaagac acggccgtgt attactgtgc gaaagatcga       300
ctctctataa caattcgccc acgctattac ggtctggacg tctggggcca agggaccacg       360
gtcaccgtct cc                                                          372

<210> SEQ ID NO 114
<211> LENGTH: 124
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Glu Gly Leu Leu Glu Gln Pro Gly Gly
 1               5                  10                  15

Ser Leu Arg Leu Ser Cys Ala Ala Ser Gly Phe Asn Phe Arg Asp Phe
                20                  25                  30

Ala Met Thr Trp Val Arg Gln Ala Pro Gly Lys Gly Leu Glu Trp Val
            35                  40                  45

Ser Ser Ile Ser Gly Ser Gly Ser Asn Thr Tyr Tyr Ala Asp Ser Val
        50                  55                  60

Lys Gly Arg Phe Thr Ile Ser Arg Asp Asn Ser Asn His Thr Leu Tyr
 65                  70                  75                  80

Leu Arg Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115
gacatccaga tgacccagtc tccatcctcc ctgtctgcat ctgtaggaga cagagtcacc    60
atcacttgcc gggcgagtca ggacattagc aattattttg cctggtatca gcagaagcca   120
gggaaagttc ctaagctcct gatctttgct gcatccactt tgcatccagg ggtcccatct   180
cggttcagtg gcagtggatc tgggacagat ttcactctca ccattcgcag cctgcagcct   240
gaagatgttg caacttatta ctgtcaaaaa tatgacagtg ccccgtacac ttttggccag   300
gggaccaagc tggagatcaa a                                             321

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Val Pro Lys Leu Leu Ile
        35                  40                  45

Phe Ala Ala Ser Thr Leu His Pro Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Val Ala Thr Tyr Tyr Cys Gln Lys Tyr Asp Ser Ala Pro Tyr
                85                  90                  95

Thr Phe Gly Gln Gly Thr Lys Leu Glu Ile Lys
            100                 105

<210> SEQ ID NO 117
<211> LENGTH: 373
<212> TYPE: DNA
<213> ORGANISM: Artificial Sequence
<220> FEATURE:
<223> OTHER INFORMATION: Synthetic

<400> SEQUENCE: 117
gaggtgcagc tggtggagtc tgggggaggc ttggtacagc ctggggggtc cctgagactc    60
tcctgtgcag cctctggatt caactttaga gactttgcca tgagctgggt ccgccaggct   120
ccagggaagg ggctgagtg gtctcagct attagtggta gtggtagtaa tacatactac    180
gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattac ggtctggacg tctggggcca agggaccacg   360
gtcaccgtct cct                                                      373

<210> SEQ ID NO 118
<211> LENGTH: 124
<212> TYPE: PRT
<213> ORGANISM: Artificial Sequence
<220> FEATURE:
<223> OTHER INFORMATION: Synthetic

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Arg Asp Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 119
<211> LENGTH: 322
<212> TYPE: DNA
<213> ORGANISM: Artificial Sequence
<220> FEATURE:
<223> OTHER INFORMATION: Synthetic

<400> SEQUENCE: 119
gacatccaga tgacccagtc tccatcctcc ctgtctgcat ctgtaggaga cagagtcacc    60
atcacttgcc gggcgagtca ggacattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaaa tatgacagtg ccccgtacac ttttggccag   300
gggaccaagc tggagatcaa ac                                            322

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Val Ala Thr Tyr Tyr Cys Gln Lys Tyr Asp Ser Ala Pro Tyr
                    85                  90                  95

Thr Phe Gly Gln Gly Thr Lys Leu Glu Ile Lys
        100                 105
```

<210> SEQ ID NO 121
<211> LENGTH: 357
<212> TYPE: DNA
<213> ORGANISM: Artificial Sequence
<220> FEATURE:
<223> OTHER INFORMATION: Synthetic

<400> SEQUENCE: 121

```
caggtgcagc tggtggagtc tgggggaggc ttggtacagc ctggggggtc cctgagactc      60
tcctgtgtag cttctggatt caccttaac aactttgtca tgaactgggt ccgccaggtt     120
ccagggaagg gactggagtg gtctcttttt attagtgcta gtggtggtag tatatactac     180
gcagactccg tgaagggccg gttcaccatc tccagagaca cttccaagaa cacattatat     240
ctgcaaatga acagcctgag agccgacgac acggccgtct attactgtgc gaaatccccg     300
tataactgga accctttga ctattggggc cagggaacca cggtcaccgt ctcctca        357
```

<210> SEQ ID NO 122
<211> LENGTH: 119
<212> TYPE: PRT
<213> ORGANISM: Artificial Sequence
<220> FEATURE:
<223> OTHER INFORMATION: Synthetic

<400> SEQUENCE: 122

```
Gln Val Gln Leu Val Glu Ser Gly Gly Gly Leu Val Gln Pro Gly Gly
  1               5                  10                  15

Ser Leu Arg Leu Ser Cys Val Ala Ser Gly Phe Thr Leu Asn Asn Phe
            20                  25                  30

Val Met Asn Trp Val Arg Gln Val Pro Gly Lys Gly Leu Glu Trp Val
        35                  40                  45

Ser Phe Ile Ser Ala Ser Gly Gly Ser Ile Tyr Tyr Ala Asp Ser Val
    50                  55                  60

Lys Gly Arg Phe Thr Ile Ser Arg Asp Thr Ser Lys Asn Thr Leu Tyr
 65                 70                  75                  80

Leu Gln Met Asn Ser Leu Arg Ala Asp Asp Thr Ala Val Tyr Tyr Cys
                85                  90                  95

Ala Lys Ser Pro Tyr Asn Trp Asn Pro Phe Asp Tyr Trp Gly Gln Gly
            100                 105                 110

Thr Thr Val Thr Val Ser Ser
        115
```

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123

```
ggattcaccc ttaacaactt tgtc                                             24
```

<210> SEQ ID NO 124
<211> LENGTH: 8
<212> TYPE: PRT

```
<213> ORGANISM: Artificial Sequence
<220> FEATURE:
<223> OTHER INFORMATION: Synthetic

<400> SEQUENCE: 124

Gly Phe Thr Leu Asn Asn Phe Val
 1               5

<210> SEQ ID NO 125
<211> LENGTH: 24
<212> TYPE: DNA
<213> ORGANISM: Artificial Sequence
<220> FEATURE:
<223> OTHER INFORMATION: Synthetic

<400> SEQUENCE: 125
attagtgcta gtggtggtag tata                                           24

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ile Ser Ala Ser Gly Gly Ser Ile
 1               5

<210> SEQ ID NO 127
<211> LENGTH: 36
<212> TYPE: DNA
<213> ORGANISM: Artificial Sequence
<220> FEATURE:
<223> OTHER INFORMATION: Synthetic

<400> SEQUENCE: 127
gcgaaatccc cgtataactg gaaccccttt gactat                              36

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Ala Lys Ser Pro Tyr Asn Trp Asn Pro Phe Asp Tyr
 1               5                   10

<210> SEQ ID NO 129
<211> LENGTH: 327
<212> TYPE: DNA
<213> ORGANISM: Artificial Sequence
<220> FEATURE:
<223> OTHER INFORMATION: Synthetic

<400> SEQUENCE: 129
gacatccagt tgacccagtc tccagccacc ctgtctgtgt ctccagggga acgagccacc    60
ctctcctgca gggccagtct gagtgttagc agcaaattag cctggtacca gcagacacct   120
ggccaggctc ccagactcct catctatagt gcctccaccc gggccactgg tatcccagtc   180
aggttcagtg gcagtgggtc tgggacagag ttcactctca ccatcagcag cctgcagtct   240
gaagattttg cggtttatta ctgtcagcag tataatcatt ggcctccgta cactttggc    300 caggggacca aggtggagat caaacga                                      327
```

<210> SEQ ID NO 130
<211> LENGTH: 109
<212> TYPE: PRT
<213> ORGANISM: Artificial Sequence
<220> FEATURE:
<223> OTHER INFORMATION: Synthetic

<400> SEQUENCE: 130

```
Asp Ile Gln Leu Thr Gln Ser Pro Ala Thr Leu Ser Val Ser Pro Gly
  1               5                  10                  15

Glu Arg Ala Thr Leu Ser Cys Arg Ala Ser Leu Ser Val Ser Ser Lys
             20                  25                  30

Leu Ala Trp Tyr Gln Gln Thr Pro Gly Gln Ala Pro Arg Leu Leu Ile
         35                  40                  45

Tyr Ser Ala Ser Thr Arg Ala Thr Gly Ile Pro Val Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn His Trp Pro Pro
                 85                  90                  95

Tyr Thr Phe Gly Gln Gly Thr Lys Val Glu Ile Lys Arg
            100                 105
```

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131
ctgagtgtta gcagcaaa                                                       18

<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

```
Leu Ser Val Ser Ser Lys
  1               5
```

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133 agtgcctcc                                                                  9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ser Ala Ser

-continued

<210> SEQ ID NO 135
<211> LENGTH: 30
<212> TYPE: DNA
<213> ORGANISM: Artificial Sequence
<220> FEATURE:
<223> OTHER INFORMATION: Synthetic

<400> SEQUENCE: 135
cagcagtata atcattggcc tccgtacact                                        30

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Gln Gln Tyr Asn His Trp Pro Pro Tyr Thr
 1               5                  10

<210> SEQ ID NO 137
<211> LENGTH: 357
<212> TYPE: DNA
<213> ORGANISM: Artificial Sequence
<220> FEATURE:
<223> OTHER INFORMATION: Synthetic

<400> SEQUENCE: 137
gaggtgcagc tggtggagtc tgggggaggc ttggtacagc ctggggggtc cctgagactc        60
tcctgtgtag cttctggatt caccctta ac aactttgtca tgaactgggt ccgccaggtt      120
ccagggaagg gactggagtg ggtctctttt attagtgcta gtggtggtag tatatactac       180
gcagactccg tgaagggccg gttcaccatc tccagagaca cttccaagaa cacattatat       240
ctgcaaatga acagcctgag agccgacgac acggccgtct attactgtgc gaaatccccg       300
tataactgga acccctttga ctattggggc cagggaaccc tggtcaccgt ctcctca         357

<210> SEQ ID NO 138
<211> LENGTH: 119
<212> TYPE: PRT
<213> ORGANISM: Artificial Sequence
<220> FEATURE:
<223> OTHER INFORMATION: Synthetic

<400> SEQUENCE: 138

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Leu Asn Asn Phe
            20                  25                  30

Val Met Asn Trp Val Arg Gln Val Pro Gly Lys Gly Leu Glu Trp Val
        35                  40                  45

Ser Phe Ile Ser Ala Ser Gly Gly Ser Ile Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Ser Pro Tyr Asn Trp Asn Pro Phe Asp Tyr Trp Gly Gln Gly
            100                 105                 110

Thr Leu Val Thr Val Ser Ser
        115

<210> SEQ ID NO 139
<211> LENGTH: 324
<212> TYPE: DNA
<213> ORGANISM: Artificial Sequence
<220> FEATURE:
<223> OTHER INFORMATION: Synthetic

<400> SEQUENCE: 139
gaaatagtga tgacgcagtc tccagccacc ctgtctgtgt ctccagggga acgagccacc    60
ctctcctgca gggccagtct gagtgttagc agcaaattag cctggtacca gcagacacct   120
ggccaggctc ccagactcct catctatagt gcctccaccc gggccactgg tatcccagtc   180
aggttcagtg gcagtgggtc tgggacagag ttcactctca ccatcagcag cctgcagtct   240
gaagattttg cggtttatta ctgtcagcag tataatcatt ggcctccgta cacttttggc   300
caggggacca agctggagat caaa                                          324

<210> SEQ ID NO 140
<211> LENGTH: 108
<212> TYPE: PRT
<213> ORGANISM: Artificial Sequence
<220> FEATURE:
<223> OTHER INFORMATION: Synthetic

<400> SEQUENCE: 140

Glu Ile Val Met Thr Gln Ser Pro Ala Thr Leu Ser Val Ser Pro Gly
  1               5                  10                  15

Glu Arg Ala Thr Leu Ser Cys Arg Ala Ser Leu Ser Val Ser Ser Lys
             20                  25                  30

Leu Ala Trp Tyr Gln Gln Thr Pro Gly Gln Ala Pro Arg Leu Leu Ile
         35                  40                  45

Tyr Ser Ala Ser Thr Arg Ala Thr Gly Ile Pro Val Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn His Trp Pro Pro
                 85                  90                  95

Tyr Thr Phe Gly Gln Gly Thr Lys Leu Glu Ile Lys
            100                 105

<210> SEQ ID NO 141
<211> LENGTH: 357
<212> TYPE: DNA
<213> ORGANISM: Artificial Sequence
<220> FEATURE:
<223> OTHER INFORMATION: Synthetic

<400> SEQUENCE: 141
gaggtgcagc tggtggagtc tgggggaggc ttggtacagc ctggggggtc cctgagactc    60
tcctgtgcag cctctggatt caccctaac aactttgtca tgagctgggt ccgccaggct   120
ccagggaagg gctggagtg gtctcagct attagtgcta gtggtggtag tatatactac   180
gcagactccg tgaagggccg gttcaccatc tccagagaca attccaagaa cacgctgtat   240
ctgcaaatga acagcctgag agccgaggac acggccgtat attactgtgc gaaatccccg   300
tataactgga ccccttttga ctattggggc caggaaccc tggtcaccgt ctcctca      357

<210> SEQ ID NO 142

```
<211> LENGTH: 119
<212> TYPE: PRT
<213> ORGANISM: Artificial Sequence
<220> FEATURE:
<223> OTHER INFORMATION: Synthetic

<400> SEQUENCE: 142

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Asn Asn Phe
             20                  25                  30

Val Met Ser Trp Val Arg Gln Ala Pro Gly Lys Gly Leu Glu Trp Val
         35                  40                  45

Ser Ala Ile Ser Ala Ser Gly Gly Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Pro Tyr Asn Trp Asn Pro Phe Asp Tyr Trp Gly Gln Gly
            100                 105                 110

Thr Leu Val Thr Val Ser Ser
        115

<210> SEQ ID NO 143
<211> LENGTH: 325
<212> TYPE: DNA
<213> ORGANISM: Artificial Sequence
<220> FEATURE:
<223> OTHER INFORMATION: Synthetic

<400> SEQUENCE: 143
gaaatagtga tgacgcagtc tccagccacc ctgtctgtgt ctccagggga aagagccacc      60
ctctcctgca gggccagtct gagtgttagc agcaaattag cctggtacca gcagaaacct     120
ggccaggctc ccaggctcct catctatagt gcctccacca gggccactgg tatcccagcc     180
aggttcagtg gcagtgggtc tgggacagag ttcactctca ccatcagcag cctgcagtct     240
gaagattttg cagtttatta ctgtcagcag tataatcatt ggcctccgta cacttttggc     300
caggggacca agctggagat caaac                                            325

<210> SEQ ID NO 144
<211> LENGTH: 108
<212> TYPE: PRT
<213> ORGANISM: Artificial Sequence
<220> FEATURE:
<223> OTHER INFORMATION: Synthetic

<400> SEQUENCE: 144

Glu Ile Val Met Thr Gln Ser Pro Ala Thr Leu Ser Val Ser Pro Gly
 1               5                  10                  15

Glu Arg Ala Thr Leu Ser Cys Arg Ala Ser Leu Ser Val Ser Ser Lys
             20                  25                  30

Leu Ala Trp Tyr Gln Gln Lys Pro Gly Gln Ala Pro Arg Leu Leu Ile
         35                  40                  45

Tyr Ser Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn His Trp Pro Pro
```

```
                85                  90                  95
Tyr Thr Phe Gly Gln Gly Thr Lys Leu Glu Ile Lys
            100                 105

<210> SEQ ID NO 145
<211> LENGTH: 375
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggaggc ttggaacagc cggggggggtc cctgagactc      60 tcctgtgcag gctctggatt cacctttaga gactatgcca tgacctgggt ccgccaggct     120
ccagggaagg gactggagtg ggtctcatct attagtggtt ccgg tggtaa cacatactac    180 gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattat ggtttggacg tctggggcca agggtccacg     360
gtcaccgtct cctca                                                      375

<210> SEQ ID NO 146
<211> LENGTH: 125
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct ttagagacta tgcc                                              24

<210> SEQ ID NO 148
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 148

Gly Phe Thr Phe Arg Asp Tyr Ala
 1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggtt ccggtggtaa caca                                            24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Ser Gly Gly Asn Thr
 1               5

<210> SEQ ID NO 151
<211> LENGTH: 54
<212> TYPE: DNA
<213> ORGANISM: Artificial Sequence
<220> FEATURE:
<223> OTHER INFORMATION: Synthetic

<400> SEQUENCE: 151
gcgaaagatc gactctctat aacaattcgc ccacgctatt atggtttgga cgtc           54

<210> SEQ ID NO 152
<211> LENGTH: 18
<212> TYPE: PRT
<213> ORGANISM: Artificial Sequence
<220> FEATURE:
<223> OTHER INFORMATION: Synthetic

<400> SEQUENCE: 152

Ala Lys Asp Arg Leu Ser Ile Thr Ile Arg Pro Arg Tyr Tyr Gly Leu
 1               5                  10                  15

Asp Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gacatcgtgt tgacccagtc tccactctcc ctgcccgtca cccctggaga gccggcctcc     60
atctcctgca ggtctagtca gagcctcctg tatagtattg gatacaacta tttggattgg   120
tacctgcaga agtcagggca gtctccacag ctccttatct atttgggttc taatcgggcc   180
tccggggtcc ctgacaggtt cagtggcagt ggatcaggca cagatttac actgaaaatc    240 agcagagtgg aggctgagga tgttgggttt tattactgca tgcaagctct acaaactccg   300
``` tacactttg gccaggggac caagctggag atcaaacga                    339

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

```
Asp Ile Val Leu Thr Gln Ser Pro Leu Ser Leu Pro Val Thr Pro Gly
 1               5                  10                  15
Glu Pro Ala Ser Ile Ser Cys Arg Ser Ser Gln Ser Leu Leu Tyr Ser
             20                  25                  30
Ile Gly Tyr Asn Tyr Leu Asp Trp Tyr Leu Gln Lys Ser Gly Gln Ser
         35                  40                  45
Pro Gln Leu Leu Ile Tyr Leu Gly Ser Asn Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Phe Tyr Tyr Cys Met Gln Ala
                 85                  90                  95
Leu Gln Thr Pro Tyr Thr Phe Gly Gln Gly Thr Lys Leu Glu Ile Lys
            100                 105                 110
Arg
```

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
cagagcctcc tgtatagtat tggatacaac tat                    33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

```
Gln Ser Leu Leu Tyr Ser Ile Gly Tyr Asn Tyr
 1               5                  10
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ttgggttct                    9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Leu Gly Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
atgcaagctc tacaaactcc gtacact                                        27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Leu Gln Thr Pro Tyr Thr
 1               5

<210> SEQ ID NO 161
<211> LENGTH: 372
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttggaacagc cggggggtc cctgagactc      60 tcctgtgcag gctctggatt cacctttaga gactatgcca tgacctgggt ccgccaggct    120
ccagggaagg gactggagtg gtctcatct attagtggtt ccggtggtaa cacatactac     180
gcagactccg tgaagggccg gttcaccatc tccagagaca attccaagaa cacgctgtat    240
ctgcaaatga acagcctgag agccgaggac acggccgtat attactgtgc gaaagatcga    300
ctctctataa caattcgccc acgctattat ggtttggacg tctggggcca agggaccacg    360
gtcaccgtct cc                                                       372

<210> SEQ ID NO 162
<211> LENGTH: 124
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Leu Glu Gln Pro Gly Gly
 1               5                  10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 163
<211> LENGTH: 336
<212> TYPE: DNA
<213> ORGANISM: Artificial Sequence
<220> FEATURE:
<223> OTHER INFORMATION: Synthetic

<400> SEQUENCE: 163

```
gacatcgtga tgacccagtc tccactctcc ctgcccgtca cccctggaga gccggcctcc      60
atctcctgca ggtctagtca gagcctcctg tatagtattg atacaacta tttggattgg     120 tacctgcaga agtcagggca gtctccacag ctccttatct atttgggttc taatcgggcc    180
tccggggtcc ctgacaggtt cagtggcagt ggatcaggca cagattttac actgaaaatc    240
agcagagtgg aggctgagga tgttgggttt tattactgca tgcaagctct acaaactccg    300 tacactttg gccaggggac caagctggag atcaaa                               336
```

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 165
<211> LENGTH: 373
<212> TYPE: DNA
<213> ORGANISM: Artificial Sequence
<220> FEATURE:
<223> OTHER INFORMATION: Synthetic

<400> SEQUENCE: 165

```
gaggtgcagc tggtggagtc tgggggaggc ttggtacagc ctgggggtc cctgagactc       60 tcctgtgcag cctctggatt cacctttaga gactatgcca tgagctgggt ccgccaggct    120
ccagggaagg ggctggagtg gtctcagct attagtggtt ccgtggtaa cacatactac      180 gcagactccg tgaagggccg gttcaccatc tccagagaca attccaagaa cacgctgtat    240
ctgcaaatga acagcctgag agccgaggac acggccgtat attactgtgc gaaagatcga    300
```

```
ctctctataa caattcgccc acgctattat ggtttggacg tctggggcca agggaccacg    360
gtcaccgtct cct                                                      373
```

<210> SEQ ID NO 166
<211> LENGTH: 124
<212> TYPE: PRT
<213> ORGANISM: Artificial Sequence
<220> FEATURE:
<223> OTHER INFORMATION: Synthetic

<400> SEQUENCE: 166

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Arg Asp Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 167
<211> LENGTH: 337
<212> TYPE: DNA
<213> ORGANISM: Artificial Sequence
<220> FEATURE:
<223> OTHER INFORMATION: Synthetic

<400> SEQUENCE: 167

```
gatattgtga tgactcagtc tccactctcc ctgcccgtca cccctggaga gccggcctcc    60
atctcctgca ggtctagtca gagcctcctg tatagtattg atacaactta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
tacacttttg gccaggggac caagctggag atcaaac                            337
```

<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Tyr Ser
             20                  25                  30

Ile Gly Tyr Asn Tyr Leu Asp Trp Tyr Leu Gln Lys Pro Gly Gln Ser
         35                  40                  45
```

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 169
<211> LENGTH: 375
<212> TYPE: DNA
<213> ORGANISM: Artificial Sequence
<220> FEATURE:
<223> OTHER INFORMATION: Synthetic

<400> SEQUENCE: 169
caggtgcagc tggtggagtc tgggggagtc ttggagcagc ctgggggtc cctgagactc      60 tcctgtacag cctctggatt cacctttaga gactatgcca tgacctgggt ccgccaggct     120
ccagggaagg ggctggagtg ggtctcatct attagtggta gtggtggtaa tacatactac     180
gcagactccg tgaggggccg gttcaccatc tccagagaca actccaacca cacgctgtat     240
ctgcaaatga acagcctgag agccgaagac acggccgtat attactgtgc gaaagatcga     300
ctctccataa caattcgccc acgctattac ggtttggacg tctggggcca agggtccacg     360
gtcaccgtct cctca                                                     375

<210> SEQ ID NO 170
<211> LENGTH: 125
<212> TYPE: PRT
<213> ORGANISM: Artificial Sequence
<220> FEATURE:
<223> OTHER INFORMATION: Synthetic

<400> SEQUENCE: 170

Gln Val Gln Leu Val Glu Ser Gly Gly Val Leu Glu Gln Pro Gly Gly
1               5                   10                  15

Ser Leu Arg Leu Ser Cys Thr Ala Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Arg Gly Arg Phe Thr Ile Ser Arg Asp Asn Ser Asn His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171

```
ggattcacct ttagagacta tgcc                                          24
```

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

```
Gly Phe Thr Phe Arg Asp Tyr Ala
1               5
```

<210> SEQ ID NO 173
<211> LENGTH: 24
<212> TYPE: DNA
<213> ORGANISM: Artificial Sequence
<220> FEATURE:
<223> OTHER INFORMATION: Synthetic

<400> SEQUENCE: 173

```
attagtggta gtggtggtaa taca                                          24
```

<210> SEQ ID NO 174
<211> LENGTH: 8
<212> TYPE: PRT
<213> ORGANISM: Artificial Sequence
<220> FEATURE:
<223> OTHER INFORMATION: Synthetic

<400> SEQUENCE: 174

```
Ile Ser Gly Ser Gly Gly Asn Thr
1               5
```

<210> SEQ ID NO 175
<211> LENGTH: 54
<212> TYPE: DNA
<213> ORGANISM: Artificial Sequence
<220> FEATURE:
<223> OTHER INFORMATION: Synthetic

<400> SEQUENCE: 175

```
gcgaaagatc gactctccat aacaattcgc ccacgctatt acggtttgga cgtc         54
```

<210> SEQ ID NO 176
<211> LENGTH: 18
<212> TYPE: PRT
<213> ORGANISM: Artificial Sequence
<220> FEATURE:
<223> OTHER INFORMATION: Synthetic

<400> SEQUENCE: 176

```
Ala Lys Asp Arg Leu Ser Ile Thr Ile Arg Pro Arg Tyr Tyr Gly Leu
1               5                   10                  15

Asp Val
```

<210> SEQ ID NO 177
<211> LENGTH: 324
<212> TYPE: DNA
<213> ORGANISM: Artificial Sequence
<220> FEATURE:
<223> OTHER INFORMATION: Synthetic

<400> SEQUENCE: 177

```
gatattgtga tgacccagtc tccatcctcc ctgtctgcat ctgtaggaga cagagtcacc    60
attacttgcc gggcgagtca ggacattagc aattattttg cctggtatca gcagaaacca   120
```

```
gggaaagttc ctaaactcct gatctttgct gcatccactt tgcatccagg ggtcccatct    180
cggttcagtg gcagtggatc tgggacagat tcactctca ccattagtag cctgcagcct    240
gaagatgttg caacttatta ctgtcaaaag tataacagtg ccccgtacac ttttggccag    300
gggaccaagg tggaaatcaa acga                                           324
```

<210> SEQ ID NO 178
<211> LENGTH: 108
<212> TYPE: PRT
<213> ORGANISM: Artificial Sequence
<220> FEATURE:
<223> OTHER INFORMATION: Synthetic

<400> SEQUENCE: 178

```
Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Val Pro Lys Leu Leu Ile
        35                  40                  45

Phe Ala Ala Ser Thr Leu His Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Val Glu Ile Lys Arg
            100                 105
```

<210> SEQ ID NO 179
<211> LENGTH: 18
<212> TYPE: DNA
<213> ORGANISM: Artificial Sequence
<220> FEATURE:
<223> OTHER INFORMATION: Synthetic

<400> SEQUENCE: 179

```
caggacatta gcaattat                                                   18
```

<210> SEQ ID NO 180
<211> LENGTH: 6
<212> TYPE: PRT
<213> ORGANISM: Artificial Sequence
<220> FEATURE:
<223> OTHER INFORMATION: Synthetic

<400> SEQUENCE: 180

```
Gln Asp Ile Ser Asn Tyr
 1               5
```

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181

```
gctgcatcc                                                              9
```

<210> SEQ ID NO 182
<211> LENGTH: 3

```
<212> TYPE: PRT
<213> ORGANISM: Artificial Sequence
<220> FEATURE:
<223> OTHER INFORMATION: Synthetic

<400> SEQUENCE: 182

Ala Ala Ser
 1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
caaaagtata acagtgcccc gtacact                                            27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Gln Lys Tyr Asn Ser Ala Pro Tyr Thr
 1               5

<210> SEQ ID NO 185
<211> LENGTH: 372
<212> TYPE: DNA
<213> ORGANISM: Artificial Sequence
<220> FEATURE:
<223> OTHER INFORMATION: Synthetic

<400> SEQUENCE: 185
gaggtgcagc tggtggagtc tgggggagtc ttggagcagc ctggggggtc cctgagactc         60
tcctgtacag cctctggatt cacctttaga gactatgcca tgacctgggt ccgccaggct        120
ccagggaagg ggctggagtg ggtctcatct attagtggta gtggtggtaa tacatactac        180
gcagactccg tgaggggccg gttcaccatc tccagagaca actccaacca cacgctgtat        240
ctgcaaatga acagcctgag agccgaagac acggccgtat attactgtgc gaaagatcga        300
ctctccataa caattcgccc acgctattac ggtttggacg tctggggcca agggaccacg        360
gtcaccgtct cc                                                            372

<210> SEQ ID NO 186
<211> LENGTH: 124
<212> TYPE: PRT
<213> ORGANISM: Artificial Sequence
<220> FEATURE:
<223> OTHER INFORMATION: Synthetic

<400> SEQUENCE: 186

Glu Val Gln Leu Val Glu Ser Gly Gly Val Leu Glu Gln Pro Gly Gly
 1               5                  10                  15

Ser Leu Arg Leu Ser Cys Thr Ala Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ser Ser Ile Ser Gly Ser Gly Gly Asn Thr Tyr Tyr Ala Asp Ser Val
     50                  55                  60
```

Arg Gly Arg Phe Thr Ile Ser Arg Asp Asn Ser Asn His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Gly Leu
            100                 105                 110

Asp Val Trp Gly Gln Gly Thr Thr Val Thr Val Ser
            115                 120

<210> SEQ ID NO 187
<211> LENGTH: 321
<212> TYPE: DNA
<213> ORGANISM: Artificial Sequence
<220> FEATURE:
<223> OTHER INFORMATION: Synthetic

<400> SEQUENCE: 187
gacatccaga tgacccagtc tccatcctcc ctgtctgcat ctgtaggaga cagagtcacc     60
attacttgcc gggcgagtca ggacattagc aattattttg cctggtatca gcagaagcca   120
gggaaagttc ctaaactcct gatctttgct gcatccactt tgcatccagg ggtcccatct   180
cggttcagtg gcagtggatc tgggacagat ttcactctca ccattagtag cctgcagcct   240
gaagatgttg caacttatta ctgtcaaaag tataacagtg ccccgtacac ttttggccag   300
gggaccaagc tggagatcaa a                                             321

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Val Pro Lys Leu Leu Ile
        35                  40                  45

Phe Ala Ala Ser Thr Leu His Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 189
<211> LENGTH: 373
<212> TYPE: DNA
<213> ORGANISM: Artificial Sequence
<220> FEATURE:
<223> OTHER INFORMATION: Synthetic

<400> SEQUENCE: 189
gaggtgcagc tggtggagtc tgggggaggc ttggtacagc ctgggggtc cctgagactc      60 tcctgtgcag cctctggatt caccttagta gactatgcca tgagctgggt ccgccaggct   120

```
ccagggaagg ggctggagtg ggtctcagct attagtggta gtggtggtaa tacatactac    180
gcagactccg tgaagggccg gttcaccatc tccagagaca attccaagaa cacgctgtat    240
ctgcaaatga acagcctgag agccgaggac acggccgtat attactgtgc gaaagatcga    300
ctctccataa caattcgccc acgctattac ggtttggacg tctggggcca agggaccacg    360
gtcaccgtct cct                                                       373
```

<210> SEQ ID NO 190
<211> LENGTH: 124
<212> TYPE: PRT
<213> ORGANISM: Artificial Sequence
<220> FEATURE:
<223> OTHER INFORMATION: Synthetic

<400> SEQUENCE: 190

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Arg Asp Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Asn Thr Tyr Tyr Ala Asp Ser Val
     50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
            115                 120
```

<210> SEQ ID NO 191
<211> LENGTH: 322
<212> TYPE: DNA
<213> ORGANISM: Artificial Sequence
<220> FEATURE:
<223> OTHER INFORMATION: Synthetic

<400> SEQUENCE: 191

```
gacatccaga tgacccagtc tccatcctcc ctgtctgcat ctgtaggaga cagagtcacc     60
atcacttgcc gggcgagtca ggacattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg ccccgtacac ttttggccag    300
gggaccaagc tggagatcaa ac                                             322
```

<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
```

```
            20                  25                  30
Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105
```

<210> SEQ ID NO 193
<211> LENGTH: 355
<212> TYPE: DNA
<213> ORGANISM: Artificial Sequence
<220> FEATURE:
<223> OTHER INFORMATION: Synthetic

<400> SEQUENCE: 193

```
gaagtgcacc tggtggaatc tgggggaggc ttggtacagc ctggcaggtc cctgagactc      60
tcctgtgagg cctctggatt cacctttgat gattatgcca tgcactgggt ccggcaagct     120
ccggggaagg gcctggaatg ggtctcaggt cttagtcgga caagtgtcag tataggctat     180
gcggactctg tgaagggccg attcaccatc tccagagaca acgccaagaa ctccctttat     240
ttggaaatga acagtctgag acctgaggac acggccttat attactgtgc aaaatggggg     300
acccgggggt attttgacta ctggggccag ggaaccctgg tcaccgtctc ctcag          355
```

<210> SEQ ID NO 194
<211> LENGTH: 118
<212> TYPE: PRT
<213> ORGANISM: Artificial Sequence
<220> FEATURE:
<223> OTHER INFORMATION: Synthetic

<400> SEQUENCE: 194

```
Glu Val His Leu Val Glu Ser Gly Gly Gly Leu Val Gln Pro Gly Arg
1               5                   10                  15

Ser Leu Arg Leu Ser Cys Glu Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Ser Arg Thr Ser Val Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Pro Glu Asp Thr Ala Leu Tyr Tyr Cys
                85                  90                  95

Ala Lys Trp Gly Thr Arg Gly Tyr Phe Asp Tyr Trp Gly Gln Gly Thr
            100                 105                 110

Leu Val Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

```
<400> SEQUENCE: 195
ggattcacct ttgatgatta tgcc                                           24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Asp Asp Tyr Ala
 1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
cttagtcgga caagtgtcag tata                                           24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Leu Ser Arg Thr Ser Val Ser Ile
 1               5

<210> SEQ ID NO 199
<211> LENGTH: 33
<212> TYPE: DNA
<213> ORGANISM: Artificial Sequence
<220> FEATURE:
<223> OTHER INFORMATION: Synthetic

<400> SEQUENCE: 199
gcaaaatggg ggacccgggg gtattttgac tac                                 33

<210> SEQ ID NO 200
<211> LENGTH: 11
<212> TYPE: PRT
<213> ORGANISM: Artificial Sequence
<220> FEATURE:
<223> OTHER INFORMATION: Synthetic

<400> SEQUENCE: 200

Ala Lys Trp Gly Thr Arg Gly Tyr Phe Asp Tyr
 1               5                  10

<210> SEQ ID NO 201
<211> LENGTH: 322
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcttcc gtgtctgcat ctgtgggaga cagagtcacc     60
```

-continued

```
atcacttgtc gggcgagtca ggatattagt atttggttag cctggtatca gcagagtcca    120
gggaaagccc ctaaactcct gatcaatgtt gcatcccgtt tgcaaagtgg ggtcccatca    180
aggttcagcg gcagtggatc tgggacagat tcactctcca ccatcaacag tctgcagcct    240
gaagattttg taacttacta ttgtcaacag gctaacagtt tcccgatcac cttcggccaa    300
gggacacgac tggcgaccaa ac                                            322
```

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Val Thr Tyr Tyr Cys Gln Gln Ala Asn Ser Phe Pro Ile
                85                  90                  95

Thr Phe Gly Gln Gly Thr Arg Leu Ala Thr Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203

```
caggatatta gtatttgg                                                  18
```

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asp Ile Ser Ile Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205

```
gttgcatcc                                                            9
```

<210> SEQ ID NO 206

```
<211> LENGTH: 3
<212> TYPE: PRT
<213> ORGANISM: Artificial Sequence
<220> FEATURE:
<223> OTHER INFORMATION: Synthetic

<400> SEQUENCE: 206

Val Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacaggcta acagtttccc gatcacc                                            27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Ala Asn Ser Phe Pro Ile Thr
 1               5

<210> SEQ ID NO 209
<211> LENGTH: 355
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtacagc ctggcaggtc cctgagactc         60
tcctgtgagg cctctggatt cacctttgat gattatgcca tgcactgggt ccggcaagct       120
ccggggaagg gcctggaatg ggtctcaggt cttagtcgga caagtgtcag tataggctat       180
gcggactctg tgaagggccg attcaccatc tccagagaca cgccaagaa ctcccttttat       240 ttggaaatga acagtctgag acctgaggac acggccttat attactgtgc aaaatggggg       300
acccgggggt attttgacta ctggggccag ggaaccctgg tcaccgtctc ctcag           355

<210> SEQ ID NO 210
<211> LENGTH: 118
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Arg
 1               5                  10                  15

Ser Leu Arg Leu Ser Cys Glu Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Leu Ser Arg Thr Ser Val Ser Ile Gly Tyr Ala Asp Ser Val
     50                  55                  60
```

```
Lys Gly Arg Phe Thr Ile Ser Arg Asp Asn Ala Lys Asn Ser Leu Tyr
 65                  70                  75                  80

Leu Glu Met Asn Ser Leu Arg Pro Glu Asp Thr Ala Leu Tyr Tyr Cys
                 85                  90                  95

Ala Lys Trp Gly Thr Arg Gly Tyr Phe Asp Tyr Trp Gly Gln Gly Thr
            100                 105                 110

Leu Val Thr Val Ser Ser
        115

<210> SEQ ID NO 211
<211> LENGTH: 322
<212> TYPE: DNA
<213> ORGANISM: Artificial Sequence
<220> FEATURE:
<223> OTHER INFORMATION: Synthetic

<400> SEQUENCE: 211
gacatccaga tgacccagtc tccatcttcc gtgtctgcat ctgtgggaga cagagtcacc      60
atcacttgtc gggcgagtca ggatattagt atttggttag cctggtatca gcagagtcca    120
gggaaagccc ctaaactcct gatcaatgtt gcatcccgtt tgcaaagtgg ggtcccatca    180
aggttcagcg gcagtggatc tgggacagat ttcactctca ccatcaacag tctgcagcct    240
gaagattttg taacttacta ttgtcaacag gctaacagtt tcccgatcac cttcggccaa    300
gggacacgac tggagattaa ac                                              322

<210> SEQ ID NO 212
<211> LENGTH: 107
<212> TYPE: PRT
<213> ORGANISM: Artificial Sequence
<220> FEATURE:
<223> OTHER INFORMATION: Synthetic

<400> SEQUENCE: 212

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Asp Ile Ser Ile Trp
             20                  25                  30

Leu Ala Trp Tyr Gln Gln Ser Pro Gly Lys Ala Pro Lys Leu Leu Ile
         35                  40                  45

Asn Val Ala Ser Arg Leu Gln Ser Gly Val Pro Ser Arg Phe Ser Gly
     50                  55                  60

Ser Gly Ser Gly Thr Asp Phe Thr Leu Thr Ile Asn Ser Leu Gln Pro
 65                  70                  75                  80

Glu Asp Phe Val Thr Tyr Tyr Cys Gln Gln Ala Asn Ser Phe Pro Ile
                 85                  90                  95

Thr Phe Gly Gln Gly Thr Arg Leu Glu Ile Lys
            100                 105

<210> SEQ ID NO 213
<211> LENGTH: 355
<212> TYPE: DNA
<213> ORGANISM: Artificial Sequence
<220> FEATURE:
<223> OTHER INFORMATION: Synthetic

<400> SEQUENCE: 213
gaagtgcagc tggtggagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt cttagtcgga caagtgtcag tataggctat    180
```

```
gcggactctg tgaagggccg attcaccatc tccagagaca acgccaagaa ctccctgtat    240
ctgcaaatga acagtctgag agctgaggac acggccttgt attactgtgc aaaatggggg    300 acccggggt attttgacta ctggggccaa ggaaccctgg tcaccgtctc ctcag          355
```

<210> SEQ ID NO 214
<211> LENGTH: 118
<212> TYPE: PRT
<213> ORGANISM: Artificial Sequence
<220> FEATURE:
<223> OTHER INFORMATION: Synthetic

<400> SEQUENCE: 214

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Leu Ser Arg Thr Ser Val Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Trp Gly Thr Arg Gly Tyr Phe Asp Tyr Trp Gly Gln Gly Thr
            100                 105                 110

Leu Val Thr Val Ser Ser
        115
```

<210> SEQ ID NO 215
<211> LENGTH: 322
<212> TYPE: DNA
<213> ORGANISM: Artificial Sequence
<220> FEATURE:
<223> OTHER INFORMATION: Synthetic

<400> SEQUENCE: 215

```
gacatccaga tgacccagtc tccatcttcc gtgtctgcat ctgtaggaga cagagtcacc    60
atcacttgtc gggcgagtca ggatattagt atttggttag cctggtatca gcagaaacca   120
gggaaagccc ctaagctcct gatctatgtt gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccgatcac cttcggccaa   300
gggacacgac tggagattaa ac                                             322
```

<210> SEQ ID NO 216
<211> LENGTH: 107
<212> TYPE: PRT
<213> ORGANISM: Artificial Sequence
<220> FEATURE:
<223> OTHER INFORMATION: Synthetic

<400> SEQUENCE: 216

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ile Trp
                20                  25                  30

Leu Ala Trp Tyr Gln Gln Lys Pro Gly Lys Ala Pro Lys Leu Leu Ile
```

```
                35                  40                  45
Tyr Val Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
            100                 105

<210> SEQ ID NO 217
<211> LENGTH: 363
<212> TYPE: DNA
<213> ORGANISM: Artificial Sequence
<220> FEATURE:
<223> OTHER INFORMATION: Synthetic

<400> SEQUENCE: 217
gaggtgcagc tgttggagtc tgggggaggc ttgctacagc cggggggtc cctgagactc      60 tcctgtgcag cctctggaat cacctttagc acctatgcca tgagctgggt ccgtcaggct    120
ccagggaggg ggctggagtg ggtctcagct attagtggta gtggtgatag cacatcctac    180
gcagactccg tgaagggccg gttcaccagc tccagagaca attccaagaa cacgctgtat    240
ctgcaaatga acagcctgag agccgaggac acggccgtat attactgtgc gaaagtcata    300
gcagctcgtc ctcactggaa cttcgatctc tggggccgtg gcaccctggt cactgtctcc    360
tca                                                                  363

<210> SEQ ID NO 218
<211> LENGTH: 121
<212> TYPE: PRT
<213> ORGANISM: Artificial Sequence
<220> FEATURE:
<223> OTHER INFORMATION: Synthetic

<400> SEQUENCE: 218

Glu Val Gln Leu Leu Glu Ser Gly Gly Gly Leu Leu Gln Pro Gly Gly
  1               5                  10                  15

Ser Leu Arg Leu Ser Cys Ala Ala Ser Gly Ile Thr Phe Ser Thr Tyr
                 20                  25                  30

Ala Met Ser Trp Val Arg Gln Ala Pro Gly Arg Gly Leu Glu Trp Val
             35                  40                  45

Ser Ala Ile Ser Gly Ser Gly Asp Ser Thr Ser Tyr Ala Asp Ser Val
 50                  55                  60

Lys Gly Arg Phe Thr Ser Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Ile Ala Ala Arg Pro His Trp Asn Phe Asp Leu Trp Gly
            100                 105                 110

Arg Gly Thr Leu Val Thr Val Ser Ser
        115                 120

<210> SEQ ID NO 219
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 219
ggaatcacct ttagcaccta tgcc                                              24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Ile Thr Phe Ser Thr Tyr Ala
1               5

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221
attagtggta gtggtgatag caca                                              24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Ser Gly Ser Gly Asp Ser Thr
1               5

<210> SEQ ID NO 223
<211> LENGTH: 42
<212> TYPE: DNA
<213> ORGANISM: Artificial Sequence
<220> FEATURE:
<223> OTHER INFORMATION: Synthetic

<400> SEQUENCE: 223
gcgaaagtca tagcagctcg tcctcactgg aacttcgatc tc                          42

<210> SEQ ID NO 224
<211> LENGTH: 14
<212> TYPE: PRT
<213> ORGANISM: Artificial Sequence
<220> FEATURE:
<223> OTHER INFORMATION: Synthetic

<400> SEQUENCE: 224

Ala Lys Val Ile Ala Ala Arg Pro His Trp Asn Phe Asp Leu
1               5                   10

<210> SEQ ID NO 225
<211> LENGTH: 324
<212> TYPE: DNA
<213> ORGANISM: Artificial Sequence
<220> FEATURE:
<223> OTHER INFORMATION: Synthetic

<400> SEQUENCE: 225
gaaattgtgt tgacacagtc tccagccacc ctgtctttgt ctccagggga aagagccacc       60
ctctcctgca gggccagtca gagtgttagt agatatttag cctggtatca acagaaacct      120
```

-continued

```
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg gagtttatta ctgtcagcag cgtagtgact ggccgctcac tttcggcgga      300
gggaccaagg tggagatcaa acgg                                              324
```

```
<210> SEQ ID NO 226
<211> LENGTH: 107
<212> TYPE: PRT
<213> ORGANISM: Artificial Sequence
<220> FEATURE:
<223> OTHER INFORMATION: Synthetic

<400> SEQUENCE: 226
```

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Gly Val Tyr Tyr Cys Gln Gln Arg Ser Asp Trp Pro Leu
                 85                  90                  95

Thr Phe Gly Gly Gly Thr Lys Val Glu Ile Lys
            100                 105

```
<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227
cagagtgtta gtagatat                                                     18

<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228
```

Gln Ser Val Ser Arg Tyr
 1               5

```
<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 gatgcatcc                                                                9

<210> SEQ ID NO 230
<211> LENGTH: 3
```

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Asp Ala Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
cagcagcgta gtgactggcc gctcact                                         27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Arg Ser Asp Trp Pro Leu Thr
 1               5

<210> SEQ ID NO 233
<211> LENGTH: 363
<212> TYPE: DNA
<213> ORGANISM: Artificial Sequence
<220> FEATURE:
<223> OTHER INFORMATION: Synthetic

<400> SEQUENCE: 233
gaggtgcagc tgttggagtc tgggggaggc ttgctacagc cggggggggtc cctgagactc      60 tcctgtgcag cctctggaat cacctttagc acctatgcca tgagctgggt ccgtcaggct     120
ccagggaggg ggctggagtg gtctcagct attagtggta gtggtgatag cacatcctac      180
gcagactccg tgaagggccg gttcaccagc tccagagaca attccaagaa cacgctgtat     240
ctgcaaatga acagcctgag agccgaggac acggccgtat attactgtgc gaaagtcata     300
gcagctcgtc ctcactggaa cttcgatctc tggggccgtg gcaccctggt cactgtctcc     360
tca                                                                  363

<210> SEQ ID NO 234
<211> LENGTH: 121
<212> TYPE: PRT
<213> ORGANISM: Artificial Sequence
<220> FEATURE:
<223> OTHER INFORMATION: Synthetic

<400> SEQUENCE: 234

Glu Val Gln Leu Leu Glu Ser Gly Gly Gly Leu Leu Gln Pro Gly Gly
 1               5                  10                  15

Ser Leu Arg Leu Ser Cys Ala Ala Ser Gly Ile Thr Phe Ser Thr Tyr
            20                  25                  30

Ala Met Ser Trp Val Arg Gln Ala Pro Gly Arg Gly Leu Glu Trp Val
        35                  40                  45

Ser Ala Ile Ser Gly Ser Gly Asp Ser Thr Ser Tyr Ala Asp Ser Val
    50                  55                  60

Lys Gly Arg Phe Thr Ser Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110

Arg Gly Thr Leu Val Thr Val Ser Ser
        115                 120

<210> SEQ ID NO 235
<211> LENGTH: 324
<212> TYPE: DNA
<213> ORGANISM: Artificial Sequence
<220> FEATURE:
<223> OTHER INFORMATION: Synthetic

<400> SEQUENCE: 235
gaaattgtgt tgacacagtc tccagccacc ctgtctttgt ctccagggga aagagccacc      60
ctctcctgca gggccagtca gagtgttagt agatatttag cctggtatca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg gagtttatta ctgtcagcag cgtagtgact ggccgctcac tttcggcgga     300
gggaccaagg tggagatcaa acgg                                            324

<210> SEQ ID NO 236
<211> LENGTH: 107
<212> TYPE: PRT
<213> ORGANISM: Artificial Sequence
<220> FEATURE:
<223> OTHER INFORMATION: Synthetic

<400> SEQUENCE: 236

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 237
<211> LENGTH: 363
<212> TYPE: DNA
<213> ORGANISM: Artificial Sequence
<220> FEATURE:
<223> OTHER INFORMATION: Synthetic

<400> SEQUENCE: 237
gaggtgcagc tgttggagtc tgggggaggc ttggtacagc cggggggtc cctgagactc       60 tcctgtgcag cctctggaat cacctttagc acctatgcca tgagctgggt ccgtcaggct     120

```
ccagggaagg ggctggagtg ggtctcagct attagtggta gtggtgatag cacatactac      180
gcagactccg tgaagggccg gttcaccatc tccagagaca attccaagaa cacgctgtat      240
ctgcaaatga acagcctgag agccgaggac acggccgtat attactgtgc gaaagtcata      300
gcagctcgtc ctcactggaa cttcgatctc tggggccgtg caccctggt cactgtctcc       360 tca                                                                    363
```

<210> SEQ ID NO 238
<211> LENGTH: 121
<212> TYPE: PRT
<213> ORGANISM: Artificial Sequence
<220> FEATURE:
<223> OTHER INFORMATION: Synthetic

<400> SEQUENCE: 238

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ile Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110

Arg Gly Thr Leu Val Thr Val Ser Ser
        115                 120
```

<210> SEQ ID NO 239
<211> LENGTH: 324
<212> TYPE: DNA
<213> ORGANISM: Artificial Sequence
<220> FEATURE:
<223> OTHER INFORMATION: Synthetic

<400> SEQUENCE: 239

```
gaaattgtgt tgacacagtc tccagccacc ctgtctttgt ctccagggga aagagccacc      60
ctctcctgca gggccagtca gagtgttagt agatatttag cctggtatca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagtgact ggccgctcac tttcggcgga    300
gggaccaagg tggagatcaa acgg                                            324
```

<210> SEQ ID NO 240
<211> LENGTH: 108
<212> TYPE: PRT
<213> ORGANISM: Artificial Sequence
<220> FEATURE:
<223> OTHER INFORMATION: Synthetic

<400> SEQUENCE: 240

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
```

```
                    20                  25                  30
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys Arg
            100                 105

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggaggc gtggtccagc ctggggaggtc cctgagactc      60 acctgtgcag cctctggatt caccttcagt agtaatggca tgcactgggt ccgccaggct     120
ccaggcaagg ggctggagtg ggtggcaatt atatcatatg atggaaataa tcaatactat     180
gcagactccg tgaagggccg attcaccatc tccagagaca attccaagca cacgctgtat     240
ctggaaatga acagcctgag agctgaggac acggctgtgt attactgtac aaaagccatc     300
tctataagtg gaacttacaa ctggttcgat tcctggggcc agggaaccct ggtcaccgtc     360
tcctca                                                                 366

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Gly Val Val Gln Pro Gly Arg
1               5                   10                  15

Ser Leu Arg Leu Thr Cys Ala Ala Ser Gly Phe Thr Phe Ser Ser Asn
            20                  25                  30

Gly Met His Trp Val Arg Gln Ala Pro Gly Lys Gly Leu Glu Trp Val
        35                  40                  45

Ala Ile Ile Ser Tyr Asp Gly Asn Asn Gln Tyr Tyr Ala Asp Ser Val
    50                  55                  60

Lys Gly Arg Phe Thr Ile Ser Arg Asp Asn Ser Lys His Thr Leu Tyr
65                  70                  75                  80

Leu Glu Met Asn Ser Leu Arg Ala Glu Asp Thr Ala Val Tyr Tyr Cys
                85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120

<210> SEQ ID NO 243
<211> LENGTH: 24
<212> TYPE: DNA
<213> ORGANISM: Artificial Sequence
```

```
<220> FEATURE:
<223> OTHER INFORMATION: Synthetic

<400> SEQUENCE: 243
ggattcacct tcagtagtaa tggc                                    24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ser Asn Gly
 1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaaataa tcaa                                    24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Asn Asn Gln
 1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
acaaaagcca tctctataag tggaacttac aactggttcg attcc              45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Thr Lys Ala Ile Ser Ile Ser Gly Thr Tyr Asn Trp Phe Asp Ser
 1               5                  10                  15

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
```

```
gaaattgtat tgacacagtc tccagccatc ctgtctttgt ctccagggga aagagccacc    60
ctctcctgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcaacag cgtagcaact ggccgctcac tttcggcgga   300
gggaccaagg tggagatcaa acgg                                          324
```

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Glu Ile Val Leu Thr Gln Ser Pro Ala Ile Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagagtgtta gcaggtac                                                  18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Val Ser Arg Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gatgcatcc                                                             9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Asp Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacagcgta gcaactggcc gctcact                                          27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Arg Ser Asn Trp Pro Leu Thr
 1               5

<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc      60
acctgtgcag cctctggatt caccttcagt agtaatggca tgcactgggt ccgccaggct     120
ccaggcaagg ggctggagtg ggtggcaatt atatcatatg atggaaataa tcaatactat     180
gcagactccg tgaagggccg attcaccatc tccagagaca attccaagca cacgctgtat     240
ctggaaatga acagcctgag agctgaggac acggctgtgt attactgtac aaaagccatc     300
tctataagtg gaacttacaa ctggttcgat cctggggcc agggaaccct ggtcaccgtc      360
tcctca                                                                366

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
 1               5                  10                  15

Ser Leu Arg Leu Thr Cys Ala Ala Ser Gly Phe Thr Phe Ser Ser Asn
             20                  25                  30

Gly Met His Trp Val Arg Gln Ala Pro Gly Lys Gly Leu Glu Trp Val
         35                  40                  45

Ala Ile Ile Ser Tyr Asp Gly Asn Asn Gln Tyr Tyr Ala Asp Ser Val
    50                  55                  60

Lys Gly Arg Phe Thr Ile Ser Arg Asp Asn Ser Lys His Thr Leu Tyr
65                  70                  75                  80

Leu Glu Met Asn Ser Leu Arg Ala Glu Asp Thr Ala Val Tyr Tyr Cys
                85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120

<210> SEQ ID NO 259
<211> LENGTH: 324
<212> TYPE: DNA
<213> ORGANISM: Artificial Sequence
<220> FEATURE:
<223> OTHER INFORMATION: Synthetic

<400> SEQUENCE: 259
gaaattgtat tgacacagtc tccagccatc ctgtctttgt ctccagggga aagagccacc      60
ctctcctgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcaacag cgtagcaact ggccgctcac tttcggcgga    300
gggaccaagg tggagatcaa acgg                                           324

<210> SEQ ID NO 260
<211> LENGTH: 107
<212> TYPE: PRT
<213> ORGANISM: Artificial Sequence
<220> FEATURE:
<223> OTHER INFORMATION: Synthetic

<400> SEQUENCE: 260

Glu Ile Val Leu Thr Gln Ser Pro Ala Ile Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 261
<211> LENGTH: 366
<212> TYPE: DNA
<213> ORGANISM: Artificial Sequence
<220> FEATURE:
<223> OTHER INFORMATION: Synthetic

<400> SEQUENCE: 261
caggtgcagc tggtggagtc tgggggaggc gtggtccagc ctgggaggtc cctgagactc      60

```
tcctgtgcag cctctggatt caccttcagt agtaatggca tgcactgggt ccgccaggct      120
ccaggcaagg ggctggagtg ggtggcagtt atatcatatg atggaaataa tcaatactat      180
gcagactccg tgaagggccg attcaccatc tccagagaca attccaagaa cacgctgtat      240
ctgcaaatga acagcctgag agctgaggac acggctgtgt attactgtac aaaagccatc      300
tctataagtg gaacttacaa ctggttcgat cctggggcc agggaaccct ggtcaccgtc      360
tcctca                                                                366
```

<210> SEQ ID NO 262
<211> LENGTH: 122
<212> TYPE: PRT
<213> ORGANISM: Artificial Sequence
<220> FEATURE:
<223> OTHER INFORMATION: Synthetic

<400> SEQUENCE: 262

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Asn
             20                  25                  30

Gly Met His Trp Val Arg Gln Ala Pro Gly Lys Gly Leu Glu Trp Val
         35                  40                  45

Ala Val Ile Ser Tyr Asp Gly Asn Asn Gln Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120
```

<210> SEQ ID NO 263
<211> LENGTH: 324
<212> TYPE: DNA
<213> ORGANISM: Artificial Sequence
<220> FEATURE:
<223> OTHER INFORMATION: Synthetic

<400> SEQUENCE: 263

```
gaaattgtat tgacacagtc tccagccacc ctgtctttgt ctccagggga aagagccacc      60
ctctcctgca gggccagtca gagtgttagc aggtacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcaacag cgtagcaact ggccgctcac tttcggcgga     300
gggaccaagg tggagatcaa acgg                                             324
```

<210> SEQ ID NO 264
<211> LENGTH: 108
<212> TYPE: PRT
<213> ORGANISM: Artificial Sequence
<220> FEATURE:
<223> OTHER INFORMATION: Synthetic

<400> SEQUENCE: 264

```
Glu Ile Val Leu Thr Gln Ser Pro Ala Thr Leu Ser Leu Ser Pro Gly
```

-continued

```
                1               5                   10                  15
Glu Arg Ala Thr Leu Ser Cys Arg Ala Ser Gln Ser Val Ser Arg Tyr
                    20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg
                100                 105

<210> SEQ ID NO 265
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 265

Xaa Xaa Xaa Xaa Xaa Xaa Xaa Xaa
1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 266

Xaa Xaa Xaa Xaa Xaa Xaa Xaa Xaa
1               5

<210> SEQ ID NO 267
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(18)
<223> OTHER INFORMATION: Xaa = Any amino acid

<400> SEQUENCE: 267

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 268
<211> LENGTH: 11
<212> TYPE: PRT
<213> ORGANISM: Artificial Sequence
<220> FEATURE:
<223> OTHER INFORMATION: Synthetic
```

```
<220> FEATURE:
<221> NAME/KEY: VARIANT
<222> LOCATION: (1)...(11)
<223> OTHER INFORMATION: Xaa = Any amino acid

<400> SEQUENCE: 268

Xaa Xaa Xaa Xaa Xaa Xaa Xaa Xaa Xaa Xaa Xaa
 1               5                  10

<210> SEQ ID NO 269
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 269

Xaa Xaa Xaa
 1

<210> SEQ ID NO 270
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 270

Xaa Xaa Xaa Xaa Xaa Xaa Xaa Xaa Xaa
 1               5

<210> SEQ ID NO 271
<211> LENGTH: 330
<212> TYPE: PRT
<213> ORGANISM: Artificial Sequence
<220> FEATURE:
<223> OTHER INFORMATION: Synthetic

<400> SEQUENCE: 271

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 272
<211> LENGTH: 327
<212> TYPE: PRT
<213> ORGANISM: Artificial Sequence
<220> FEATURE:
<223> OTHER INFORMATION: Synthetic

<400> SEQUENCE: 272

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 273
<211> LENGTH: 327
<212> TYPE: PRT
<213> ORGANISM: Artificial Sequence
<220> FEATURE:
<223> OTHER INFORMATION: Synthetic

<400> SEQUENCE: 273

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
            210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 274
<211> LENGTH: 207
<212> TYPE: PRT
<213> ORGANISM: Homo sapiens

<400> SEQUENCE: 274

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
                20                  25                  30

Leu Arg Leu Leu Tyr Gln Leu Val Phe Leu Leu Ser Glu Ala His Thr
            35                  40                  45

Cys Ile Pro Glu Asn Asn Gly Gly Ala Gly Cys Val Cys His Leu Leu
        50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
                100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
        130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 275
<211> LENGTH: 231
<212> TYPE: PRT
<213> ORGANISM: Macaca fasicularis

<400> SEQUENCE: 275

Met Gly Trp Leu Cys Ser Gly Leu Leu Phe Pro Val Ser Cys Leu Val
1               5                   10                  15
```

```
Leu Leu Gln Val Ala Ser Ser Gly Ser Met Lys Val Leu Gln Glu Pro
            20              25              30
Thr Cys Val Ser Asp Tyr Met Ser Ile Ser Thr Cys Glu Trp Lys Met
            35              40              45
Gly Gly Pro Thr Asn Cys Ser Ala Glu Leu Arg Leu Leu Tyr Gln Leu
    50              55              60
Val Phe Gln Ser Ser Glu Thr His Thr Cys Val Pro Glu Asn Asn Gly
65              70              75              80
Gly Val Gly Cys Val Cys His Leu Leu Met Asp Asp Val Val Ser Met
            85              90              95
Asp Asn Tyr Thr Leu Asp Leu Trp Ala Gly Gln Gln Leu Leu Trp Lys
            100             105             110
Gly Ser Phe Lys Pro Ser Glu His Val Lys Pro Arg Ala Pro Gly Asn
        115             120             125
Leu Thr Val His Thr Asn Val Ser Asp Thr Val Leu Leu Thr Trp Ser
    130             135             140
Asn Pro Tyr Pro Pro Asp Asn Tyr Leu Tyr Asn Asp Leu Thr Tyr Ala
145             150             155             160
Val Asn Ile Trp Ser Glu Asn Asp Pro Ala Tyr Ser Arg Ile His Asn
            165             170             175
Val Thr Tyr Leu Lys Pro Thr Leu Arg Ile Pro Ala Ser Thr Leu Lys
            180             185             190
Ser Gly Ile Ser Tyr Arg Ala Arg Val Arg Ala Trp Ala Gln His Tyr
        195             200             205
Asn Thr Thr Trp Ser Glu Trp Ser Pro Ser Thr Lys Trp Tyr Asn Ser
    210             215             220
Tyr Arg Glu Pro Phe Glu Gln
225             230
```

HIGH AFFINITY HUMAN ANTIBODIES TO HUMAN IL-4 RECEPTOR

CROSS-REFERENCE TO RELATED APPLICATIONS

This application is a divisional of U.S. patent application Ser. No. 13/287,151, filed on Nov. 2, 2011, issued as U.S. Pat. No. 8,337,839, which is a divisional of U.S. patent application Ser. No. 12/556,605, filed on Sep. 10, 2009, issued as U.S. Pat. No. 8,075,887, which is a divisional of U.S. patent application Ser. No. 12/260,307, filed on Oct. 29, 2008, issued as U.S. Pat. No. 7,608,693, which is a continuation-in-part of U.S. patent application Ser. No. 11/906,517, filed on Oct. 2, 2007, issued as U.S. Pat. No. 7,605,237, which claims the benefit under 35 USC §119(e) of U.S. Provisional Application No. 60/848,694, filed on Oct. 2, 2006, and U.S. Provisional Application No. 60/957,738, filed on Aug. 24, 2007, the contents of which are herein specifically incorporated by reference in their entireties.

BACKGROUND

Interleukin-4 (IL-4, also known as B cell stimulating factor or BSF-1) was originally characterized by its ability to stimulate the proliferation of B cells in response to low concentrations of antibodies directed to surface immunoglobulin. IL-4 has been shown to possess a broad spectrum of biological activities, including growth stimulation of T cells, mast cells, granulocytes, megakaryocytes and erythrocytes. IL-4 induces the expression of class II major histocompatibility complex molecules in resting B cells, and enhances the secretion of IgE and IgG1 isotypes by stimulated B cells.

The biological activities of IL-4 are mediated by specific cell surface receptors for IL-4. Human IL-4 receptor alpha (hIL-4R) (SEQ ID NO:274) is described in, for example, U.S. Pat. Nos. 5,599,905, 5,767,065, and 5,840,869. Antibodies to hIL-4R are described in U.S. Pat. Nos. 5,717,072 and 7,186,809.

Methods to produce antibodies useful as human therapeutics include generating chimeric antibodies and humanized antibodies (see, for example, U.S. Pat. No. 6,949,245). See, for example, WO 94/02602 and U.S. Pat. No. 6,596,541 (both of which publications are herein specifically incorporated by reference) describing methods of generating nonhuman transgenic mice capable of producing human antibodies.

Methods for using antibodies to hIL-4R are described in U.S. Pat. Nos. 5,714,146, 5,985,280; and 6,716,587.

BRIEF SUMMARY OF THE INVENTION

In a first aspect, the invention provides human antibodies, preferably recombinant human antibodies, that specifically bind human interleukin-4 receptor (hIL-4R). The human antibodies are characterized by binding to hIL-4R with high affinity and by the ability to neutralize hIL-4 activity. In specific embodiments, the human antibodies are capable of blocking hIL-13/hIL-13R1 complex binding to hIL-4R, and thus inhibit signaling by hIL-13. The antibodies can be full-length (for example, an IgG1 or IgG4 antibody) or may comprise only an antigen-binding portion (for example, a Fab, F(ab')$_2$ or scFv fragment), and may be modified to effect functionality, e.g., to eliminate residual effector functions (Reddy et al. (2000) J. Immunol, 164:1925-1933).

In a general embodiment, the invention provides an antibody or antigen-binding fragment thereof, that specifically binds hIL-4R (SEQ ID NO:274) with a $K_D$ of about 300 pM or less, as measured by surface plasmon resonance in a monomeric or dimeric assay. In a more specific embodiment, the antibody or antigen-binding portion thereof exhibits a $K_D$ of about 200 pM or less, about 150 or less, about 100 pM or less, or about 50 pM. In various embodiments, the antibody or antigen-binding fragment blocks hIL-4 activity with an $IC_{50}$ of about 100 pM or less, as measured by luciferase bioassay. In more specific embodiments, the antibody or antigen-binding fragment exhibits an $IC_{50}$ of about 50 pM or less, about 30 pM or less, or about 25 pM or less, as measured by STAT6 luciferase bioassay. In various embodiments, the antibody or antigen-binding fragment blocks hIL-13 activity with an $IC_{50}$ of about 100 pM or less, about 90 pM or less, about 50 pM or less, or about 20 pM or less, as measured by STAT6 luciferase bioassay.

In a second aspect, the antibody of the invention comprises a heavy chain variable region (HCVR) sequence selected from the group consisting of SEQ ID NO:2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258 and 262, or a substantially similar sequence thereof.

In a third aspect, the antibody of the invention comprises a light chain variable region (LCVR) sequence selected from the group consisting of SEQ ID NO:10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260 and 264, or a substantially similar sequence thereof.

in one embodiment, the antibody or antibody fragment of the invention comprises HCVR and LCVR sequence pairs (HCVR/LCVR) selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260 and 262/264. In a preferred embodiment, the antibody or antibody fragment comprise HCVR/LCVR sequence pairs SEQ ID NO:162/164, 210/212 and 18/20. In an even more preferred embodiment, the antibody or antibody fragment comprises HCVR/LCVR SEQ ID NO:162/164.

In a fourth aspect, the invention provides nucleic acid molecules encoding an HCVR, wherein the nucleic acid molecule is a nucleotide sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257 and 261, or a substantially identical sequence having at least 95% homology thereof.

In a fifth aspect, the invention provides nucleic acid molecules encoding a LCVR, wherein the nucleic acid molecule is a sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259 and 263, or a substantially identical sequence having at least 95% homology thereof.

In one embodiment, the antibody of the invention comprises a HCVR and LCVR encoded by a nucleotide sequence pairs selected from the group consisting of SEQ ID NO: 1/9, 17/19, 21/22, 25/33, 41/43, 45/47, 49/57, 65/67, 69/71, 73/81, 89/91, 93/95, 97/105, 113/115, 117/119, 121/129, 137/139, 141/143, 145/153, 161/163, 165/167, 169/177, 185/187, 189/191, 193/201, 209/211, 213/215, 217/225, 233/235, 237/239, 241/249, 257/259 and 261/263. In a preferred embodiment, the antibody or antibody fragment comprise HCVR/LCVR sequences encoded by nucleic acid sequences selected from SEQ ID NO:161/163, 209/211 and 17/19. In an even more preferred embodiment, the antibody or antibody fragment comprises HCVR/LCVR encoded by nucleic acid sequences SEQ ID NO:161/163.

In a sixth aspect, the invention provides an antibody or antigen-binding fragment comprising a HCDR3 and a LCDR3, wherein the HCDR3 domain selected from the group consisting of SEQ ID NO:8, 32, 56, 80, 104, 128, 152, 176, 200, 224 and 248; and the LCDR3 domain selected from the group consisting of SEQ ID NO:16, 40, 64, 88, 112, 136, 160, 184, 208, 232 and 256. In a preferred embodiment, the HCDR3/LCDR3 sequences are SEQ ID NO:152/160, 8/16 or 200/208. In an even more preferred embodiment, the HCDR3 and LCDR3 sequences are SEQ ID NO: 152 and 160.

In a further embodiment, the antibody or antibody fragment further comprises a HCDR1 sequence selected from the group consisting of SEQ ID NO:4, 28, 52, 76, 100, 124, 148, 172, 196, 220 and 244, or a substantially similar sequence thereof; a HCDR2 sequence selected from the group consisting of SEQ ID NO:6, 30, 54, 78, 102, 126, 150, 174, 198, 222 and 246, or a substantially similar sequence thereof; a HCDR3 sequence selected from the group consisting of SEQ ID NO:8, 32, 56, 80, 104, 128, 152, 176, 200, 224 and 248; or a substantially similar sequence thereof; a LCDR1 sequence selected from the group consisting of SEQ ID NO:12, 36, 60, 84, 108, 132, 156, 180, 204, 228 and 252, or a substantially similar sequence thereof; a LCDR2 sequence selected from the group consisting of SEQ ID NO:14, 38, 62, 86, 110, 134, 158, 182, 206, 230 and 252, or a substantially similar sequence thereof; and a LCDR3 sequence selected from the group consisting of SEQ ID NO:16, 40, 64, 88, 112, 136, 160, 184, 208, 232 and 256 or a substantially similar sequences thereof. In a preferred embodiment, the antibody or antigen-binding fragment comprise HCDR sequences SEQ ID NO:148, 150 and 152 and LCDR sequences SEQ ID NO:156, 158 and 160; HCDR sequences SEQ ID NO:4, 6 and 8 and LCDR sequences SEQ ID NO:12, 14 and 16; and HCDR sequences SEQ ID NO:196, 198 and 200 and LCDR sequences SEQ ID NO:204, 206 and 208.

in a seventh aspect, the invention features a human antibody or antibody fragment comprising a HCDR3 and LCDR3, wherein the HCDR3 is encoded by a nucleotide sequence selected from the group consisting of SEQ ID NO:7, 31, 55, 79, 103, 127, 151, 175, 199, 223 and 247, or a substantially identical sequence having at least 95% homology thereof; and the LCDR3 is encoded by a nucleotide sequence selected from the group consisting of SEQ ID NO:15, 39, 63, 87, 111, 135, 159, 183, 207, 231 and 255, or a substantially identical sequence having at least 95% homology thereof.

In a further embodiment, the invention features a human antibody or antibody fragment comprising a HCDR1 domain encoded by a nucleotide sequence selected from the group consisting of SEQ ID NO:3, 27, 51, 75, 99, 123, 147, 171, 195, 219 and 243, or a substantially identical sequence having at least 95% homology thereof; a HCDR2 domain encoded by a nucleotide sequence selected from the group consisting of SEQ ID NO:5, 29, 53, 77, 101, 125, 149, 173, 197, 221 and 245, or a substantially identical sequence having at least 95% homology thereof; a HCDR3 domain encoded by a nucleotide sequence selected from the group consisting of SEQ ID NO: 7, 31, 55, 79, 103, 127, 151, 175, 199, 223 and 247, or a substantially similar sequence having at least 95% homology thereof; a LCDR1 domain encoded by a nucleotide sequence selected from the group consisting of SEQ ID NO:11, 35, 59, 83, 107, 131, 155, 179, 203, 227 and 251, or a substantially similar sequence having at least 95% homology thereof; a LCDR2 domain encoded by a nucleotide sequence selected from the group consisting of SEQ ID NO:13, 37, 61, 85, 109, 133, 157, 181, 205, 229 and 253, or a substantially similar sequence having at least 95% homology thereof; and LCDR3 domain encoded by a nucleotide sequence selected from the group consisting of SEQ ID NO: 15, 39, 63, 87, 111, 135, 159, 183, 207, 231 and 255, or a substantially similar sequence having at least 95% homology thereof. In a preferred embodiment, the antibody or antigen-binding fragment comprise HCDR and LCDR sequences encoded by nucleotide sequences SEQ ID NO:147, 149, 151, 155, 157 and 159; 195, 197, 199, 203, 205 and 207; and 3, 5, 7, 11, 13 and 15.

In a specific embodiment, the anti-hIL-4R antibody or antigen-binding fragment of the invention comprises HCVR comprising the amino acid sequence shown in SEQ ID NO:162 and LCVR comprising the amino acid sequence shown in SEQ ID NO:164, and is characterized by a $K_D$ of about 100 pM or less (monomeric substrate) or 70 pM or less (dimeric substrate); a $K_D$ of about 160 pM or less (monomeric substrate) or 40 pM or less (dimeric substrate) at 25° C. and 37° C., respectively; and an $IC_{50}$ of about 10 pM or less (25 pM dimer substrate) or about 100 pM or less (200 pM monomer substrate), which is capable of blocking both hIL-4 and hIL-13 activity with an $IC_{50}$ of about 30 pM or less (as measured by bioassay) and cross-reacts with monkey IL-4R.

In a specific embodiment, the anti-hIL-4R antibody or antigen-binding fragment of the invention comprises HCVR comprising the amino acid sequence shown in SEQ ID NO:18 and LCVR comprising the amino acid sequence shown in SEQ ID NO:20, and is characterized by a $K_D$ of about 450 pM or less (monomeric or dimeric substrate); and an $IC_{50}$ of about 40 pM or less (25 pM dimer substrate) or about 100 pM or less (200 pM monomer substrate), which is capable of blocking both hIL-4 and hIL-13 activity with an $IC_{50}$ of about 100 pM or less (as measured by bioassay).

In a specific embodiment, the anti-hIL-4R antibody or antigen-binding fragment of the invention comprises HCVR comprising the amino acid sequence shown in SEQ ID NO:210 and LCVR comprising the amino acid sequence shown in SEQ ID NO:212, and is characterized by a $K_D$ of about 50 pM or less (monomeric substrate) or 30 pM or less (dimeric substrate); a $K_D$ of about 200 pM or less (monomeric substrate) or 40 pM or less (dimeric substrate) at 25° C. and 37° C., respectively; and an $IC_{50}$ of about 10 pM or less (25 pM dimer substrate) or about 90 pM or less (200 pM monomer substrate), which is capable of blocking both hIL-4 and hIL-13 activity with an $IC_{50}$ of about 25 pM or less (as measured by bioassay) and does not cross-reacts with monkey IL-4R.

In a eighth aspect, the invention features an antibody or antigen-binding fragment of an antibody that specifically binds hIL-4R, comprising three heavy chain and three light chain complementarity determining regions (HCDR1, HCDR2, HCDR3, LCDR1, LCDR2, LCDR3), wherein the HCDR1 comprises an amino acid sequence of the formula $X^1$-$X^2$-$X^3$-$X^4$-$X^5$-$X^6$-$X^7$-$X^8$ (SEQ ID NO:265), wherein $X^1$=Gly; $X^2$=Phe; $X^3$=Thr; $X^4$=Phe; $X^5$=Asp or Arg; $X^6$=Asp or Ser; $X^7$=Tyr; and $X^8$=Ala or Gly; the HCDR2 comprises an amino acid sequence of the formula $X^1$-$X^2$-$X^3$-$X^4$-$X^5$-$X^6$-$X^7$-$X^8$ (SEQ ID NO:266), wherein $X^1$=Ile or Leu, $X^2$=Ser, $X^3$=Gly, Tyr or Arg, $X^4$=Ser, Asp or Thr, $X^5$=Gly or Ser, $X^6$=Gly, Ser or Val, $X^7$=Ser or Asn, and $X^8$=Thr, Lys or Ile; the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:267) wherein $X^1$=Ala, $X^2$=Lys, $X^3$=Asp, Glu or Trp, $X^4$=Gly or Arg, $X^5$=Leu, Thr or Arg, $X^6$=Gly, Arg or Ser, $X^7$=Ile or Gly, $X^8$=Thr, Phe or Tyr, $X^9$=Ile, Asp or Phe, $X^{10}$=Arg, Tyr or Asp, $X^{11}$=Pro, Tyr or absent, $X^{12}$=Arg or absent, $X^{13}$=Tyr or absent, $X^{14}$=Tyr or absent, $X^{15}$=Gly or absent, $X^{16}$=Leu or absent, $X^{17}$=Asp or absent, and $X^{18}$=Val or absent; the LCDR1 comprises an amino acid sequence of the formula $X^1$-$X^2$-$X^3$-$X^4$-$X^5$-$X^6$-$X^7$-$X^8$-$X^9$-$X^{10}$-$X^{11}$ (SEQ ID NO:268) wherein $X^1$=Gln, $X^2$=Asp, Ser or Val, $X^3$=Ile or Leu, $X^4$=Ser, Leu or Asn, $X^5$=Asn, Tyr or Ile, $X^6$=Trp, Ser or Tyr; $X^7$=Ile or absent; $X^8$=Gly or absent; $X^9$=Tyr or absent; $X^{10}$=Asn or absent; and $X^{11}$=Tyr or absent; the LCDR2 comprises an amino acid sequence of the formula $X^1$-$X^2$-$X^3$ (SEQ ID NO:269) wherein $X^1$=Leu, Ala or Val, $X^2$=Ala or Gly, and $X^3$=Ser; and the LCDR3 comprises an amino acid sequence of the formula $X^1$-$X^2$-$X^3$-$X^4$-$X^5$-$X^6$-$X^7$-$X^8$-$X^9$ (SEQ ID NO:270) wherein $X^1$=Gln or Met, $X^2$=Gln, $X^3$=Ala or Tyr, $X^4$=Leu or Asn, $X^5$=Gln or Ser, $X^6$=Thr, Phe or His, $X^7$=Pro, $X^8$=Tyr, Ile or Trp, and $X^9$=Thr.

In a more specific embodiment, the HCDR1 comprises an amino acid sequence of the formula $X^1$-$X^2$-$X^3$-$X^4$-$X^5$-$X^6$-$X^7$-$X^8$ (SEQ ID NO:265), wherein $X^1$=Gly; $X^2$=Phe; $X^3$=Thr; $X^4$=Phe; $X^5$=Arg; $X^6$=Asp or Ser; $X^7$=Tyr; and $X^8$=Ala or Gly; the HCDR2 comprises an amino acid sequence of the formula $X^1$-$X^2$-$X^3$-$X^4$-$X^5$-$X^6$-$X^7$-$X^8$ (SEQ ID NO:266), wherein $X^1$=Ile, $X^2$=Ser, $X^3$=Gly or Tyr, $X^4$=Ser or Thr, $X^5$=Gly, $X^6$=Gly or Ser, $X^7$=Asn, and $X^8$=Ser or Lys; the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:267) wherein $X^1$=Ala, $X^2$=Lys, $X^3$=Asp or Glu, $X^4$=Gly or Arg, $X^5$=Leu or Arg, $X^6$=Gly or Ser, $X^7$=Ile or Gly, $X^8$=Thr or Phe, $X^9$=Ile or Asp, $X^{10}$=Arg or Tyr, $X^{11}$=Pro or absent, $X^{12}$=Arg or absent, $X^{13}$=Tyr or absent, $X^{14}$=Tyr or absent, $X^{15}$=Gly or absent, $X^{16}$Leu or absent, $X^{17}$=Asp or absent, and $X^{18}$=Val or absent, the LCDR1 comprises an amino acid sequence of the formula $X^1$-$X^2$-$X^3$-$X^4$-$X^5$-$X^6$-$X^7$-$X^8$-$X^9$-$X^{10}$-$X^{11}$ (SEQ ID NO:268) wherein $X^1$=Gln, $X^2$=Ser or Val, $X^3$=Ile or Leu, $X^4$=Leu or Asn, $X^5$=Asn or Tyr, $X^6$=Ser or Tyr; $X^7$=Ile or absent; $X^8$=Gly or absent; $X^9$=Tyr or absent; $X^{10}$=Asn or absent; and $X^{11}$=Tyr or absent; the LCDR2 comprises an amino acid sequence of the formula $X^1$-$X^2$-$X^3$ (SEQ ID NO:269) wherein $X^1$=Leu or Ala, $X^2$=Ala or Gly, and $X^3$=Ser; and the LCDR3 comprises an amino acid sequence of the formula $X^1$-$X^2$-$X^3$-$X^4$-$X^5$-$X^6$-$X^7$-$X^8$-$X^9$ (SEQ ID NO:270) wherein $X^1$=Gln or Met, $X^2$=Gln, $X^3$=Ala or Tyr, $X^4$=Leu or Asn, $X^5$=Gln or Ser, $X^6$=Thr or His, $X^7$=Pro, $X^8$=Tyr or Trp, and $X^9$=Thr.

In another more specific embodiment, the HCDR 1 comprises an amino acid sequence of the formula $X^1$-$X^2$-$X^3$-$X^4$-$X^5$-$X^6$-$X^7$-$X^8$ (SEQ ID NO:265), wherein $X^1$=Gly; $X^2$=Phe; $X^3$=Thr; $X^4$=Phe; $X^5$=Asp or Arg; $X^6$=Asp; $X^7$=Tyr; and $X^8$=Ala; the HCDR2 comprises an amino acid sequence of the formula $X^1$-$X^2$-$X^3$-$X^4$-$X^5$-$X^6$-$X^7$-$X^8$ (SEQ ID NO:266), wherein $X^1$=Ile or Leu, $X^2$=Ser, $X^3$=Gly or Arg, $X^4$=Ser or Thr, $X^5$=Gly or Ser, $X^6$=Gly or Val, $X^7$=Ser or Asn, and $X^8$=Thr or Ile; the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:267) wherein $X^1$=Ala, $X^2$=Lys, $X^3$=Asp or Trp, $X^4$=Gly or Arg, $X^5$=Leu or Thr, $X^6$=Arg or Ser, $X^7$=Ile or Gly, $X^8$=Thr or Tyr, $X^9$=Ile or Phe, $X^{10}$=Arg or Asp, $X^{11}$=Pro, Tyr or absent, $X^{12}$=Arg or absent, $X^{13}$=Tyr or absent, $X^{14}$=Tyr or absent, $X^{15}$=Gly or absent, $X^{16}$=Leu or absent, $X^{17}$=Asp or absent, and $X^{18}$=Val or absent; the LCDR1 comprises an amino acid sequence of the formula $X^1$-$X^2$-$X^3$-$X^4$-$X^5$-$X^6$-$X^7$-$X^8$-$X^9$-$X^{10}$-$X^{11}$ (SEQ ID NO:268) wherein $X^1$=Gln, $X^2$=Asp or Ser, $X^3$=Ile or Leu, $X^4$=Ser or Leu, $X^5$=Tyr or Ile, $X^6$=Trp or Ser; $X^7$=Ile or absent; $X^8$=Gly or absent; $X^9$=Tyr or absent; $X^{10}$=Asn or absent; and $X^{11}$=Tyr or absent; the LCDR2 comprises an amino acid sequence of the formula $X^1$-$X^2$-$X^3$ (SEQ ID NO:269) wherein $X^1$=Leu or Val, $X^2$=Ala or Gly, and $X^3$=Ser; and the LCDR3 comprises an amino acid sequence of the formula $X^1$-$X^2$-$X^3$-$X^4$-$X^5$-$X^6$-$X^7$-$X^8$ (SEQ ID NO:270) wherein $X^1$=Gln or Met, $X^2$=Gln, $X^3$=Ala, $X^4$=Leu or Asn, $X^5$=Gln or Ser, $X^6$=Thr or Phe, $X^7$=Pro, $X^8$=Tyr or Ile, and $X^9$=Thr.

In a ninth aspect, the invention provides an antibody or antigen-binding fragment comprising HCDR1/HCDR2/HCDR3/LCDR1/LCDR2/LCDR3 sequences from a HCVR and LCVR pair, wherein the HCVR/LCVR sequences are selected from the group consisting of SEQ ID NO:162/164, 210/212 and 18/20, in a more specific embodiment, heavy and light chain CDR sequences are those contained in HCVR SEQ ID NO:162 and LCVR SEQ ID NO:164. In another more specific embodiment, heavy and light chain CDR sequences are those contained in HCVR SEQ ID NO:18 and LCVR SEQ ID NO:20. In yet another specific embodiment, heavy and light chain CDR sequences are those contained in HCVR SEQ ID NO:210 and LCVR SEQ ID NO:212.

The invention encompasses anti-hIL-4R antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of a galactosylation can be made in order to modify complement dependent cytotoxicity (CDC).

In a tenth aspect, the invention provides recombinant expression vectors carrying the nucleic acid molecules of the invention, and host cells into which such vectors have been included, as are methods of making the antibodies or antigen-binding fragments of the invention obtained by culturing the host cells of the invention. The host cell may be a prokaryotic or eukaryotic cell, preferably the host cell is an *E. coli* cell or a mammalian cell, such as a CHO cell.

In an eleventh aspect, the invention features a composition comprising a recombinant human antibody that specifically binds hIL-4R and an acceptable carrier.

in a twelfth aspect, the invention features methods for inhibiting hIL-4 activity using an antibody, or antigen-binding portion thereof, of the invention. In specific embodiments, the antibodies of the invention also block hIL-13/hIL-13R1 complex binding to hIL-4R. In one embodiment, the method comprises contacting hIL-4R with the antibody of the invention, or antigen-binding portion thereof, such that hIL-4 or hIL-4/hIL-13 activity is inhibited. In another embodiment, the method comprises administering an antibody of the invention, or antigen-binding portion thereof, to a human subject suffering from a disorder that is ameliorated by inhibition of hIL-4 or hIL-4/hIL-13 activity. The disorder treated is any disease or condition that is improved, ameliorated, inhibited or prevented by removal, inhibition or reduction of hIL-4 or hIL-4/hIL-13 activity.

IL-4 related disorders which are treated by the antibodies or antibody fragments of the invention include, for example, arthritis (including septic arthritis), herpetiformis, chronic idiopathic urticaria, scleroderma, hypertrophic scarring, Whipple's Disease, benign prostate hyperplasia, lung disorders, such as mild, moderate or severe asthma, inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis.

Other objects and advantages will become apparent from a review of the ensuing detailed description.

DETAILED DESCRIPTION

Before the present methods are described, it is to be understood that his invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

DEFINITIONS

The term "human IL4R" (hIL-4R), as used herein, is intended to refer to a human cytokine receptor that specifically binds interleukin-4 (IL-4), IL-4Rα (SEQ ID NO:274). The term "human interleukin-13" (hIL-13) refers to a cytokine that specifically binds IL-13 receptor, and "hIL-13/hIL-13R1 complex" refers to the complex formed by hIL-13 binding to hIL-13R1 complex, which complex binds hIL-4 receptor to initiate biological activity.

The term "antibody", as used herein, is intended to refer to immunoglobulin molecules comprising four polypeptide chains, two heavy (H) chains and two light (L) chains interconnected by disulfide bonds. Each heavy chain comprises a heavy chain variable region (HCVR or VH) and a heavy chain constant region. The heavy chain constant region comprises three domains, CH1, CH2 and CH3. Each light chain comprises a light chain variable region (LCVR or VL) and a light chain constant region. The light chain constant region comprises one domain (CL1). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion" or "antibody fragment"), as used herein, refers to one or more fragments of an antibody that retain the ability to specifically bind to an antigen (e.g., hIL-4R). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL1 and CH1 domains; (ii) a F(ab')$_2$ fragment, a bivalent fragment comprising two F(ab)' fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain; and (vi) an CDR. Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883. Such single chain antibodies are also intended to be encompassed within the term "antigen-binding portion" of an antibody. Other forms of single chain antibodies, such as diabodies, are also encompassed (see e.g., Holliger et al. (1993) Proc. Natl. Acad Sci. USA 90:6444-6448).

A "neutralizing" or "blocking" antibody, as used herein, is intended to refer to an antibody whose binding to hIL-4R results in inhibition of the biological activity of hIL-4 and/or hIL-13. This inhibition of the biological activity of hIL-4 and/or IL-13 can be assessed by measuring one or more indicators of hIL-4 and/or hIL-13 biological activity known to the art, such as hIL-4- and/or IL-13-induced cellular activation and hIL-4 binding to hIL-4R (see examples below).

A "CDR" or complementarity determining region is a region of hypervariability interspersed within regions that are more conserved, termed "framework regions" (FR). In different embodiments of the anti-hIL-4R antibody or fragment of the invention, the FRs may be identical to the human germline sequences, or may be naturally or artificially modified.

The term "surface plasmon resonance", as used herein, refers to an optical phenomenon that allows for the analysis of real-time interactions by detection of alterations in protein concentrations within a biosensor matrix, for example using the BIACORE™ system (Pharmacia Biosensor AB).

The term "epitope" is an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and, more preferably at least about 96%, 97%, 98% or 99% of the nucleotide bases, as measured by any well-known algorithm of sequence identity, such as FASTA, BLAST or Gap, as discussed below.

As applied to polypeptides, the term "substantial similarity" or "substantially similar" means that two peptide sequences, when optimally aligned, such as by the programs GAP or BESTFIT using default gap weights, share at, least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to venous substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another, preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each of which is herein incorporated by reference.

Preparation of Human Antibodies

Methods for generating human antibodies include those described in, for example, U.S. Pat. No. 6,596,541, Green et al. (1994) Nature Genetics 7:13-21), U.S. Pat. Nos. 5,545,807, 6,787,637.

Rodents can be immunized by any method known in the art (see, for example, Harlow and Lane (1988) *Antibodies: A Laboratory Manual* 1988 Cold Spring Harbor Laboratory; Malik and Lillehoj (1994) Antibody Techniques, Academic Press, CA). Antibodies of the invention are preferably prepared with the use of VELOCIMMUNE™ technology (U.S. Pat. No. 6,596,541). A transgenic mouse in which the endogenous immunoglobulin heavy and light chain variable regions are replaced with the corresponding human variable regions is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable regions of the light and heavy chains may be isolated directly from antigen-specific lymphocytes.

The DNA encoding the variable regions of the heavy and light chains of the antibody are isolated and operably linked to DNA encoding the human heavy and light chain constant regions. The DNA is then expressed in a cell capable of expressing the fully human antibody. In a specific embodiment, the cell is a CHO cell.

Antibodies may be therapeutically useful in blocking a ligand-receptor interaction or inhibiting receptor component interaction, rather than by killing cells through fixation of complement (complement-dependent cytotoxicity) (CDC) and participation antibody-dependent cell-mediated cytotoxicity (ADCC). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

Human immunoglobulins can exist in two forms that are associated with hinge heterogeneity. In one form, an immunoglobulin molecule comprises a stable four-chain construct of approximately 150-160 kDa in which the dimers are held together by an interchain heavy chain disulfide bond. In a second form, the dimers are not linked via interchain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. In fact, a single amino acid substitution in the hinge region of the human IgG4 hinge can significantly reduce the appearance of the second form (Angal et al. (1993) Molecular Immunology 30: 105) to levels typically observed using a human IgG1 hinge. The instant invention encompasses antibodies having one or more mutations in the hinge, CH2 or CH3 region that may be desirable, for example, in production, to improve the yield of the desired antibody form.

Initially, high affinity chimeric antibodies are isolated having a human variable region and a mouse constant region. As described below, the antibodies are characterized and selected for, desirable characteristics, including binding affinity to hIL-4R, ability to block hIL-4 binding to hIL-4R, and/or selectivity for the human protein. The mouse constant regions are replaced with desired human constant regions to generate the fully human antibodies of the invention, for example wild-type or modified IgG4 or IgG1 (for example, SEQ ID NO:271, 272, 273). While the constant region selected may vary according to specific use, high affinity antigen-binding and target specificity characteristics reside in the variable region.

Epitope Mapping and Related Technologies

To screen for antibodies that bind to a particular epitope, a routine cross-blocking assay such as that described in Harlow and Lane supra can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science: 9:487-496).

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US Patent Application Publication No. 2004/0101920, herein specifically incorporated by reference in its entirety). Each category may reflect a unique epitope either distinctly different from, or partially overlapping with, an epitope represented by another category. This technology allows rapid filtering of genetically identical antibodies, such that characterization can be focused on genetically distinct antibodies. When applied to hybridoma screening, MAP may facilitate identification of rare hybridoma clones with desired characteristics. MAP may be used to sort the hIL-4R antibodies of the invention into groups of antibodies binding different epitopes.

Agents useful for altering the structure of the immobilized antigen are enzymes, such as, for example, proteolytic enzymes and chemical agents. The antigen protein may be immobilized on either biosensor chip surfaces or polystyrene beads. The latter can be processed with, for example, an assay such as a multiplex LUMINEX™ detection assay (Luminex Corp., TX). Because of the capacity of LUMINEX™ to handle multiplex analysis with up to 100 different types of beads, LUMINEX™ provides almost unlimited antigen surfaces with various modifications, resulting in improved resolution in antibody epitope profiling over a biosensor assay.

Bispecifics

The antibodies of the present invention may be monospecific, bispecific, or multispecific. Multispecific antibodies may be specific for different epitopes of one target polypeptide or may contain antigen-binding domains specific for more than one target polypeptide. See, e.g., Tutt et al. (1991) J. Immunol. 147:60-69. The human anti-IL-4R antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

Therapeutic Administration and Formulations

The invention provides therapeutic compositions comprising the anti-IL-4R antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with IL-4R, in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the seventy of the condition, the frequency and the duration of the treatment can be adjusted.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of infectious Disease and Cancer, Lopez Berestein and Fidler (eds.), Liss, New York, pp. 353-365; Lopez-Berestein, ibid., pp. 317-327; see generally ibid.

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used (see Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984). Other controlled release systems are discussed in the review by Langer (1990) Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 600 mg per dosage form in a unit dose; especially in the form of injection, it is preferred that the aforesaid antibody is contained in about 5 to 100 mg and in about 10 to 250 mg for the other dosage forms.

Single and Combination Therapies.

The antibodies and antibody fragments of the invention are useful for treating diseases and disorders which are improved, inhibited or ameliorated by reducing IL-4 activity. These disorders include those characterized by abnormal or excess expression of IL-4, or by an abnormal host response to IL-4 production. IL-4 related disorders which are treated by the antibodies or antibody fragments of the include, for example, arthritis (including septic arthritis), herpetiformis, chronic idiopathic urticaria, scleroderma, hypertrophic scarring, Whipple's Disease, benign prostate hyperplasia, pulmonary disorders such as asthma (mild, moderate or severe), inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, atopic dermatitis, ulcerative colitis, fibrosis, and nephrosis (see U.S. Pat. No. 7,186,809, herein specifically incorporated by reference).

The invention encompasses combination therapies in which the anti-IL-4R antibody or antibody fragment is administered in combination with a second therapeutic agent. Co-administration and combination therapy are not limited to simultaneous administration, but include treatment regimens in which an anti-IL-4R antibody or antibody fragment is administered at least once during a course of treatment that involves administering at least one other therapeutic agent to the patient. A second therapeutic agent may be another IL-4 antagonist, such as another antibody/antibody fragment, or a soluble cytokine receptor, an IgE antagonist, an anti-asthma medication (corticosteroids, non-steroidal agents, beta agonists, leukotriene antagonists, xanthines, fluticasone, salmeterol, albuterol) which may be delivered by inhalation or other appropriate means. In a specific embodiment, the anti-IL-4R antibody or antibody fragment of the invention may be administered with an IL-1 antagonist, such as rilonacept, or an IL-13 antagonist. The second agent may include one or more leukotriene receptor antagonists to treat disorders such as allergic inflammatory diseases, e.g., asthma and allergies. Examples of leukotriene receptor antagonists include but are not limited to montelukast, pranlukast, and zafirlukast. The second agent may include a cytokine inhibitor such as one or more of a TNF (etanercept, ENBREL™), IL-9, IL-5 or IL-17 antagonist.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-4 Receptor

VELOCIMMUNE™ mice (Regeneron Pharmaceuticals, Inc.; U.S. Pat. No. 6,596,541) were immunized with human IL-4R (hIL-4R, SEQ ID NO:274) or a combination of hIL-4R and monkey (*Macaca fascicularis*) IL-4R (mfIL-4R, SEQ ID NO:275) protein or DNA. To obtain optimal immune response, animals were subsequently boosted every 3-4 weeks and bleeds obtained 10 days after each boost for assessment of progression of anti-antigen response.

When the mice attained maximum immune response, antibody-expressing B cells were harvested and fused with mouse myeloma cells to form hybridomas. Alternatively, antigen-specific antibodies may be isolated directly from the B cells without fusion to myeloma cells, as described in U.S. Patent Publication 2007/0280945A1, herein specifically incorporated by reference in its entirety. Stable recombinant antibody-expressing CHO cell lines were established from the isolated proper recombinants. Functionally desirable monoclonal antibodies were selected by screening conditioned media of the hybridomas or transfected cells for specificity, antigen-binding affinity, and potency in blocking hIL-4 binding to hIL-4R (described below).

Example 2

Antigen Binding Affinity Determination

Binding affinity ($K_D$) of selected antibodies with respect to hIL-4R at either 25° C. or 37° C. was determined using a real-time biosensor surface plasmon resonance assay (BIACORE™ 2000). Briefly, antibody was captured on a goat anti-hFc polyclonal antibody surface created through direct coupling to a BIACORE™ chip to form a captured antibody surface. Various concentrations (ranging from 50 nM to 12.5 nM) of monomeric hIL-4R (R&D Systems) or dimeric hIL-4R-mFc were injected over the captured antibody surface at 10 μl/min for 2.5 min at either 25° C. or 37° C. Binding of antigen to antibody and dissociation of the bound complex, were monitored in real time. Equilibrium dissociation constants ($K_D$) and dissociation rate constants were ascertained by performing kinetic analysis using BIA evaluation software. BIA evaluation software was also used to calculate the half-life of antigen/antibody complex dissociation ($T_{1/2}$). Results are shown in Table 1. NB: No antibody-antigen binding was observed under the experimental condition. Control, a fully human anti-IL-4R antibody (U.S. Pat. No. 7,186,809; SEQ ID NOs:10 and 12).

TABLE 1

|  | 25° C. | | | | 37° C. | | | |
| --- | --- | --- | --- | --- | --- | --- | --- | --- |
|  | Monomeric | | Dimeric | | Monomeric | | Dimeric | |
| Antibody | $K_D$ (pM) | $T_{1/2}$ (min) | $K_D$ (pM) | $T_{1/2}$ (min) | $K_D$ (pM) | $T_{1/2}$ (min) | $K_D$ (pM) | $T_{1/2}$ (min) |
| Control | 1100 | 18 | 94 | 186 | 3970 | 4 | 114 | 158 |
| H4H083P | 48 | 361 | 28 | 245 | 183 | 87 | 38.1 | 163 |

TABLE 1-continued

|  | 25° C. | | | | 37° C. | | | |
| --- | --- | --- | --- | --- | --- | --- | --- | --- |
|  | Monomeric | | Dimeric | | Monomeric | | Dimeric | |
| Antibody | $K_D$ (pM) | $T_{1/2}$ (min) | $K_D$ (pM) | $T_{1/2}$ (min) | $K_D$ (pM) | $T_{1/2}$ (min) | $K_D$ (pM) | $T_{1/2}$ (min) |
| H4H094P | NB | — | NB | — | NB | — | NB | — |
| H4H095P | 274 | 131 | 302 | 156 | 437 | 49 | 314 | 116 |
| H4H098P | 94.1 | 243 | 67.6 | 237 | 157 | 129 | 38.8 | 158 |
| H4H099P | NB | — | NB | — | NB | — | NB | — |

Binding affinity ($K_D$) of selected antibodies with respect to monkey (*Macaca fascicularis*) IL-4R (mfIL-4R) at either 25° C. or 37° C. was also determined using a real-time biosensor surface plasmon resonance assay described above with various concentrations (ranging from 100 nM to 25 nM) of monomeric mfIL-4R-myc-myc-his (mfIL-4R-mmh) or dimeric mfIL-4R-mFc. Only antibody H4H098P was able to bind both monomeric and dimeric mfIL-4R at 25° C. with $K_D$ of 552 nM and 9.08 nM, respectively. In addition, antibody H4H098P also binds to dimeric mfIL-4R at 37° C. with a $K_D$ of 24.3 nM. H4H083P had very weak binding to dimeric mfIL-4R.

Antibody-antigen binding affinity was also assessed using an ELISA-based solution competition assay. Briefly, a 96-well MAXISORP™ plate was first coated with 5 μg/ml avidin overnight followed by BSA blocking for 1 hr. The avidin-coated plate was then incubated with 250 ng/ml biotin-hIL4 for 2 hr. The plate was used to measure either free hIL-4R-mFc (dimeric hIL-4R) or free hIL-4R-myc-myc-his (hIL4R-mmh, monomeric hIL4R) in the antibody titration sample solutions. To make the antibody titration sample, a constant amount either 25 pM of hIL-4R-mFc or 200 pM of hIL-4R-mmh was premixed with varied amounts of antibody, ranging from 0 to about 10 nM in serial dilutions, followed by 1 hr incubation at room temperature to allow antibody-antigen-binding to reach equilibrium. The equilibrated sample solutions were then transferred to the hIL-4 coated plates for measurement of either free hIL-4R-mFc or free hIL-4R-mmh. After 1 hr binding, the plate was washed and bound hIL-4R-mFc was detected using either an HRP-conjugated mouse anti-mFc polyclonal antibody or an HRP-conjugated goat anti-myc polyclonal antibodies. $IC_{50}$ values were determined (Table 2).

The ELISA-based solution competition assay was also used to determine the cross reactivity of the antibodies to monkey IL-4R. Antibody H4H098P exhibits an $IC_{50}$ for mfIL-4R-mFc of 300 pM and an $IC_{50}$ for mfIL-4R-mmh of 20 nM.

Example 3

Neutralization of Biological Effect of hIL-4 and hIL-13 In Vitro

A bioassay was developed to determine the purified anti-hIL-4R antibodies to neutralize hIL-4R-mediated cellular function in vitro using an engineered HK293 cell line that contains human STAT6 and a STAT6 luciferase reporter. Inhibition of hIL-4R-inducible luciferase activity was determined as follows: Cells were seeded onto 96-well plates at $1 \times 10^4$ cells/well in media and incubated overnight at 37° C., 5% $CO_2$. Antibody proteins ranging from 0 to 20 nM in serial dilutions were added to the cells along with either 10 pM hIL-4 or 40 pM of hIL-13. Cells were then incubated at 37° C., 5% $CO_2$ for 6 hrs. The extent of cellular response was measured in a luciferase assay (Promega Biotech). Results are shown in Table 3. NB: Luciferase activity was not blocked under the experimental condition described above. In addition, H4H098P was able to block mfIL-4R-mediated cellular function in the presence of 360 fM mfIL-4 with an $IC_{50}$ of 150 nM.

TABLE 2

|  | $IC_{50}$ (pM) | |
| --- | --- | --- |
| Antibody | 25 pM hIL-4R-mFc | 200 pM hIL-4R-mmh |
| Control | 8.2 | 87 |
| H4H083P | 9.6 | 80 |
| H4H094P | >10,000 | >10,000 |
| H4H095P | 40 | 90 |
| H4H098P | 8.8 | 74 |
| H4H099P | >10,000 | >10,000 |

TABLE 3

|  | $IC_{50}$ (pM) | |
| --- | --- | --- |
| Antibody | 10 pM hIL-4 | 40 pM hIL-13 |
| Control | 47 | 38 |
| H4H083P | 25 | 19 |
| H4H094P | NB | NB |
| H4H095P | 98 | 86 |
| H4H098P | 27 | 25 |
| H4H099P | NB | 11,000 |

The invention claimed is:

1. An isolated nucleic acid molecule comprising a nucleic acid sequence encoding a heavy chain immunoglobulin variable domain region (HCVR) of an antibody that binds human interleukin-4 receptor, wherein the HCVR comprises a heavy chain CDR1 (HCDR1) comprising SEQ ID NO:148, a heavy chain CDR2 (HCDR2) comprising SEQ ID NO:150, and a heavy chain CDR3 (HCDR3) comprising SEQ ID NO:152.

2. The nucleic acid molecule of claim 1, wherein the HCVR comprises the amino acid sequence of SEQ ID NO:162.

3. The nucleic acid molecule of claim 1, wherein the HCVR comprises an HCDR1 encoded by the nucleotide sequence of SEQ ID NO:147, an HCDR2 encoded by the nucleotide sequence of SEQ ID NO:149, and an HCDR3 encoded by the nucleotide sequence of SEQ ID NO:151.

4. The nucleic acid molecule of claim 1, wherein the nucleic acid molecule comprises the nucleotide sequence of SEQ ID NO:161 or a substantially identical sequence having at least 95% homology thereof.

5. The nucleic acid molecule of claim 1, wherein the nucleic acid molecule comprises the nucleotide sequence of SEQ ID NO:161.

6. An isolated nucleic acid molecule comprising a nucleic acid sequence encoding a light chain immunoglobulin variable region (LCVR) of an antibody that binds human interleukin-4 receptor, wherein the LCVR comprises a light chain CDR1 (LCDR1) comprising SEQ ID NO:156, a light chain CDR2 (LCDR2) comprising SEQ ID NO:158, and a light chain CDR3 (LCDR3) comprising SEQ ID NO:160.

7. The nucleic acid molecule of claim 6, wherein the LCVR comprises SEQ ID NO:164.

8. The nucleic acid molecule of claim 6, wherein the LCVR comprises an LCDR1 encoded by the nucleotide sequence of SEQ ID NO:155, an LCDR2 encoded by the nucleotide sequence of SEQ ID NO:157, and an LCDR3 encoded by the nucleotide sequence of SEQ ID NO: 159.

9. The nucleic acid molecule of claim 6, wherein the nucleic acid molecule comprises the nucleotide sequence of SEQ ID NO:163 or a substantially identical sequence having at least 95% homology thereof.

10. The nucleic acid molecule of claim 6, wherein the nucleic acid molecule comprises the nucleotide sequence of SEQ ID NO:163.

11. An expression vector comprising:
    (a) a nucleic acid molecule comprising a nucleic acid sequence encoding a heavy chain immunoglobulin variable domain region (HCVR) of an antibody that binds human interleukin-4 receptor, wherein the HCVR comprises a heavy chain CDR1 (HCDR1) comprising SEQ ID NO:148, a heavy chain CDR2 (HCDR2) comprising SEQ ID NO:150, and a heavy chain CDR3 (HCDR3) comprising SEQ ID NO:152; and/or
    (b) a nucleic acid molecule comprising a nucleic acid sequence encoding a light chain immunoglobulin variable region (LCVR) of an antibody that binds human interleukin-4 receptor, wherein: the LCVR comprises a light chain CDR1 (LCDR1) comprising SEQ ID NO:156, a light chain CDR2 (LCDR2) comprising SEQ ID NO:158, and a light chain CDR3 (LCDR3) comprising SEQ ID NO:160.

12. An isolated host cell comprising the expression vector of claim 11.

13. The host cell of claim 12, wherein the host cell is a mammalian cell or a prokaryotic cell.

14. The host cell of claim 12, wherein the host cell is a Chinese Hamster Ovary (CHO) cell or an *Escherichia coli* (*E. coli*) cell.

15. A method of producing an anti-human interleukin-4 receptor antibody or antigen-binding fragment thereof, the method comprising growing the host cell of claim 12 under conditions permitting production of the antibody or antigen-binding fragment thereof, wherein said host cell comprises both a nucleic acid molecule comprising a nucleic acid sequence encoding said HCVR and a nucleic acid molecule comprising a nucleic acid sequence encoding said LCVR.

16. The method of claim 15, further comprising formulating the antibody or antigen-binding fragment thereof as a pharmaceutical composition comprising an acceptable carrier.

17. A composition comprising a first nucleic acid molecule and a second nucleic acid molecule;
wherein the first nucleic acid molecule comprises a nucleic acid sequence encoding a heavy chain immunoglobulin variable region (HCVR) of an antibody that specifically binds to human interleukin-4 receptor that comprises a heavy chain CDR1 (HCDR1) comprising SEQ ID NO:148, a heavy chain CDR2 (HCDR2) comprising SEQ ID NO:150, and a heavy chain CDR3 (HCDR3) comprising SEQ ID NO:152; and
wherein the second nucleic acid molecule comprises a nucleic acid sequence encoding a light chain immunoglobulin variable region (LCVR) of an antibody that specifically binds to human interleukin-4 receptor that comprises a light chain CDRI (LCDR1) comprising SEQ ID NO:156, a light chain CDR2 (LCDR2) comprising SEQ ID NO:158, and a light chain CDR3 (LCDR3) comprising SEQ ID NO: 160.

18. The composition of claim 17, wherein the HCVR comprises SEQ ID NO:162, and wherein the LCVR comprises SEQ ID NO:164.

19. An isolated nucleic acid molecule encoding an antibody or antigen-binding fragment thereof, which specifically binds human interleukin-4 receptor, wherein the antibody or antigen-binding fragment comprises a heavy chain variable region (HCVR) comprising three heavy chain CDRs (HCDR1, HCDR2 and HCDR3) from SEQ ID NO:162, and a light chain variable region (LCVR) comprising three light chain CDRs (LCDR1, LCDR2 and LCDR3) from SEQ ID NO:164.

20. The nucleic acid molecule of claim 19, wherein:
(a) the HCDR1 comprises SEQ ID NO:148;
(b) the HCDR2 comprises SEQ ID NO:150;
(c) the HCDR3 comprises SEQ ID NO:152;
(d) the LCDRI comprises SEQ ID NO:156;
(e) the LCDR2 comprises SEQ ID NO:158; and
(f) the LCDR3 comprises SEQ ID NO:160.

21. The nucleic acid molecule of claim 19, wherein the HCVR comprises SEQ ID NO:162.

22. The nucleic acid molecule of claim 19, wherein the LCVR comprises SEQ ID NO:164.

23. The nucleic acid molecule of claim 19, wherein the HCVR comprises SEQ ID NO:162 and the LCVR comprises SEQ ID NO:164.

24. An expression vector comprising the nucleic acid molecule of claim 19.

25. An isolated host cell comprising the expression vector of claim 24.

26. The host cell of claim 25, wherein the host cell is a mammalian cell or a prokaryotic cell.

27. The host cell of claim 25 wherein the host cell is a Chinese Hamster Ovary (CHO) cell or an *Escherichia coli* (*E. coli*) cell.

28. A method of producing an anti-human intedeukin-4 receptor antibody or antigen-binding fragment thereof, comprising growing the host cell of claim 25 under conditions permitting production of the antibody or fragment, and recovering the antibody or fragment so produced.

29. The method of claim 28, further comprising formulating the antibody or antigen-binding fragment thereof as a pharmaceutical composition comprising an acceptable carrier.

* * * * *

UNITED STATES PATENT AND TRADEMARK OFFICE
CERTIFICATE OF CORRECTION

PATENT NO. : 8,735,095 B2
APPLICATION NO. : 13/678650
DATED : May 27, 2014
INVENTOR(S) : Joel H. Martin et al.

Page 1 of 1

It is certified that error appears in the above-identified patent and that said Letters Patent is hereby corrected as shown below:

On the Title Page

Item [72], INVENTORS, Line 6, insert the text --George D. Yancopoulos, Yorktown Heights, NY (US)--

Signed and Sealed this
Seventeenth Day of March, 2020

Andrei Iancu
*Director of the United States Patent and Trademark Office*

UNITED STATES PATENT AND TRADEMARK OFFICE
CERTIFICATE OF CORRECTION

PATENT NO. : 8,735,095 B2  Page 1 of 1
APPLICATION NO. : 13/678650
DATED : May 27, 2014
INVENTOR(S) : Joel H. Martin et al.

It is certified that error appears in the above-identified patent and that said Letters Patent is hereby corrected as shown below:

In the Claims

Column 161, Line 37, Claim 17: "CDRI (LCDR1)" should read -- CDR1 (LCDR1) --.

Column 162, Line 15, Claim 20(d): "the LCDRI" should read -- the LCDR1 --.

Column 162, Line 34, Claim 28: "intedeukin-4" should read -- interleukin-4 --.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*